United States Patent
Kim et al.

(10) Patent No.: US 7,285,277 B2
(45) Date of Patent: *Oct. 23, 2007

(54) ANTICANCER AGENT

(75) Inventors: Jang-Seong Kim, Suwon-si (KR);
Jin-Hyung Ahn, Yongin-si (KR);
Hyun-Kyung Yu, Yongin-si (KR);
Ho-Jeong Lee, Yongin-si (KR);
Doo-Hong Park, Seoul (KR); Yeup Yoon, Gwacheon-si (KR)

(73) Assignee: Mogam Biotechnology Research Institute, Yongin-si, Gyeonggi-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 11/162,817

(22) Filed: Sep. 23, 2005

(65) Prior Publication Data

US 2006/0013823 A1    Jan. 19, 2006

Related U.S. Application Data

(63) Continuation-in-part of application No. 10/849,961, filed on May 19, 2004, now Pat. No. 7,118,905, which is a continuation of application No. 10/088,548, filed on Mar. 15, 2002, now Pat. No. 6,743,428.

(51) Int. Cl.
*A61K 39/00* (2006.01)
*A61K 38/03* (2006.01)
(52) U.S. Cl. ..................... 424/185.1; 514/12; 530/324
(58) Field of Classification Search ............. 424/185.1; 514/12; 530/324
See application file for complete search history.

(56) References Cited

U.S. PATENT DOCUMENTS

| | | | |
|---|---|---|---|
| 5,639,725 A | 6/1997 | O'Reily et al. | |
| 5,801,012 A | 9/1998 | Soff et al. | |
| 5,801,146 A * | 9/1998 | Davidson ..................... | 514/12 |
| 5,945,403 A | 8/1999 | Folkman et al. | |
| 6,743,428 B1 * | 6/2004 | Chang et al. ............ | 424/185.1 |
| 7,118,905 B2 * | 10/2006 | Chang et al. ............ | 435/252.3 |

FOREIGN PATENT DOCUMENTS

WO    WO 2004/073730 A1    9/2004

OTHER PUBLICATIONS

Mikol V, et al., 1996, Crystal structures of apolipoprotein(a) kringle IV37 free and complexed with 6-aminohexanoic acid and with p-aminomethylebenzoid acid: existence of novel and expected binding modes. J Mol Biol. 256(4):751-61.

Burgess et al., 1990, Possible dissociation of the heparin-binding and mitogenic activities of heparin-binding growth factor-1 from its receptor-binding activites by site-directed mutagenesis of a single lysine residue. J Cell Biol. 111:2129-2138.

Bowie Ju et al., 1990, Deciphering the message in protein sequences: tolerance to amino acid substitutions. Science. 247 (4948):1306-1310.

Fogarty M., 2002, Learning from Angiogenesis Trial Failures. The Scientist 16:33.

Fan TP et al., 1995, Controlling the vasculature: angiogenesis, anti-angiogenesis and vascular targeting of gene therapy. Trends Pharmacol Sci. 16:57-66.

Wallace RW, 1998, Media hype and drug discovery Drug Discovery Today, 3(10):433-434.

Cao Y et al., 1997, Kringle 5 of plasminogen is a novel inhibitor of endothelial cell growth. J Biol Chem. 272:22924-22928.

Kraft HG et al., 1995, Sequence polymorphism in kringle IV 37 in linkage disequilibrium with the aopolipoprotein (a) size polymorphism Hum Genet. 95(3):275-282.

McLean et al., 1987, cDNA sequence of human apolipoprotein(a) is homologous to plaminogen. Nature 330(6144):132-7.

Lou, X. J. et al., 1998, Despite Its Homology to Angiostatin Apolipoprotein(a) Does Not Affect Angiogenesis, Exp. Mol. Pathol., 65:53-63.

LoGrasso, P. V. et al., 1994, Cloning, Expression, and Characterization of Human Apolipoprotein (a) Kringle IV37, J. Biol. Chem., 269(34):21820-21827.

Scanu, A. M. and Edelstein, C., 1994, Apolipoprotein(a): structural and functional consequences of mutations in kringle type 10 (or kringle 4-37), Clinical Genetics, 46:42-45.

Scanu, A. M. et al., 1994, A single point mutation (Trp 72 à Arg) in human apo (a) kringle 4-37 associated with a lysine binding defect in Lp(a), Biochimica et Biophysica Acta, 1227:41-45.

Gabel, B. R. and Koschinsky, M. L., 1998, Sequences within Apolipoprotein(a) Kringle IV Types 6-8 Bind Directly to Low-Density Lipoprotein and Mediate Noncovalent Assocation of Apolipoprotein(a) and Apolipoprotein B-100, Biochemistry, 37:7892-7898.

* cited by examiner

*Primary Examiner*—Maher M. Haddad
(74) *Attorney, Agent, or Firm*—JHK Law; Joseph Hyosuk Kim

(57) ABSTRACT

The present application discloses a method of reducing tumor growth that includes contacting the tumor with a tumor growth reducing effective amount of a composition comprising LK8 or LK68 protein or a functionally equivalent amino acid variant thereof and a pharmaceutically acceptable carrier thereof to a subject having tumor.

18 Claims, 23 Drawing Sheets

(A)

(B)

A

B

C

D

ANTICANCER AGENT

CROSS-REFERENCE TO RELATED APPLICATIONS

The present application is a continuation in part of U.S. application Ser. No. 10/849,961, filed May 19, 2004, now U.S. Pat. No. 7,118,905, which is a continuation application Ser. No. of 10/088,548, filed Mar. 15, 2002, now U.S. Pat. No. 6,743,428B1.

BACKGROUND OF THE INVENTION

1. Field of the Invention

The present invention relates to reducing blood vessel count, reducing tumor volume including primary tumor volume, and preventing metastasis. The invention also relates to a method of treating cancer. The invention further relates to combination cancer therapy using LK8 and/or LK68.

2. General Background and State of the Art

A tumor is developed by uncontrollable, disordered, and abnormal cell proliferation. If this tumor shows a destructive growth, invasiveness and metastasis, it is regarded as a malignant tumor. Invasiveness is a character to infiltrate or destroy surrounding tissues. In particular, a basal layer forming a boundary of tissues is destroyed by the character, resulting in the local spread and sometimes inflow of a tumor through the circulatory system. Metastasis means the spread of tumor cells from the site of origin to other areas through lymphatic or blood vessels. In a broad sense, metastasis also means the direct extension of tumor cells through serous body cavity or other space.

Surgical operation, radiotherapy and chemotherapy are used for the treatment of a cancer, either alone or in combination. Surgical operation is a way to remove diseased tissues. Thus, tumors in specific regions such as breast, colon and skin can be effectively removed by surgical operation. However, a tumor in vertebra or dispersive tumor like leukemia cannot be properly treated by the surgical operation.

Chemotherapy blocks cell replication or metabolism, and has been used for the treatment of breast cancer, lung cancer and testicular cancer. However, patients with cancer who have been treated by chemotherapy have seriously suffered from the side effects of systemic chemotherapy. Motion sickness and vomiting are common. Dose-limiting toxicity (DLT) is also one of the major side effects of chemotherapy, which draws a careful attention in the administration of a medicine. Mucositis is an example of DLT against anticancer agents such as 5-fluoruracil (5-FU) which is an antimetabolic cytotoxic agent, methotrexate, and anticancer antibiotics like doxorubicin. If a patient suffers seriously from such side effects of chemotherapy, he or she should be hospitalized and given an anodyne for reducing pain. Thus, the side effects of chemotherapy and radiotherapy are the biggest problems for the treatment of cancer patients. Another major problem with current cytotoxic chemotherapy is drug resistance, in part because the malignant cells are genetically unstable and heterogeneous. The emergence of drug-resistant cancer cells may limit the long-term treatment of cytotoxic chemotherapeutic agents. Therefore, there is an urgent need to develop an anticancer agent without substantial side effects such as systemic cytotoxicity and drug resistance of the chemotherapeutic agents.

Tumor growth essentially requires the formation of new blood vessels (a process known as angiogenesis) to supply tumors with nutrients and oxygen, and allow the removal of waste products. Moreover, metastatic spread of solid tumors depends on vascularization of the primary mass. Therefore, blockage of tumor angiogenesis may potentially suppress both tumor growth and metastasis. In this regard, the angiogenic process is a promising target to develop novel therapeutic modalities for the treatment of cancer. Therefore, in one aspect, the invention is directed to an anticancer agent for treating cancer and also preventing metastasis.

Kringle is a kind of a protein structure which is composed of ~80 amino acids and three intramolecular disulfide bonds. Kringle structure is found in many proteins such as prothrombin (Walz, D. A. et al., Proc. Natl. Acad. Sci., 74:1069-1073, 1977), urokinase (Pennica, D. et al., Nature, 301:579-582, 1983), interstitial cell growth factor (Lukker, N. A. et al., Protein Eng., 7:895-903, 1 994), and apolipoprotein(a) (refered as 'apo(a)' hereinafter) (McLean, J. W. et al., Nature, 330:132-137, 1987) and appears to be an independent folding unit. However, the functions of kringle have not been clearly explained, yet.

Apo(a) includes two types of kringle regions, KIV and KV, and an inactive protease-like region. The kringle region KIV is divided into 10 subtypes (KIV-1~KIV-10) according to the homology of amino acids, and 15~40 copy numbers of the region are found in various human alleles of the apo(a) gene. Apo(a) forms a lipoprotein(a) (referred as 'Lp(a)' hereinafter) by covalent bond with apo B-100, a major protein component of low-density lipoprotein (LDL) (Fless, G. M., J. Biol. Chem., 261:8712-8717, 1986). The increase of Lp(a) content in plasma is a major risk factor of artherosclerosis (Armstrong, V. W. et al., Artherosclerosis, 62:249-257, 1986; Assmann, G., Am. J. Cardiol., 77:1179-1184, 1996).

The present inventors have studied the anticancer activity of the human apo(a) kringles. As a result, the present inventors have completed this invention by confirming that apo(a) kringle KV38 or KIV36-KIV37-KV38 can be effectively used as an anticancer agent because it inhibits angiogenesis by an endogenous growth factor like bFGF which is necessary for cancer cell growth.

SUMMARY OF THE INVENTION

It is an object of this invention to provide an anticancer and/or an antimetastasis agent comprising a human apo(a) kringle KV38 (referred as 'LK8 protein' hereinafter) or KIV36-KIV37-KV38 (referred as 'LK68 protein' hereinafter) as an active ingredient.

In one aspect, the present invention is directed to a method of reducing tumor growth comprising contacting the tumor with a tumor growth reducing effective amount of a composition comprising LK8 or LK68 protein or a functionally equivalent amino acid variant thereof and a pharmaceutically acceptable carrier thereof to a subject having tumor. The tumor may be carcinoma such as prostate cancer, melanoma, colon cancer, rectal cancer, liver cancer or lung cancer. The tumor may be a primary tumor. Further, the effective amount of LK8 or LK68 protein may be a dose of 0.1 to 100 mg/kg, or a dose of 1 to 50 mg/kg.

In another aspect of the invention, the present invention is directed to a method for inhibiting metastasis of cancer comprising administering a metastasis inhibition effective amount of a composition comprising LK8 or LK68 protein or a functionally equivalent amino acid variant thereof and a pharmaceutically acceptable carrier thereof to a subject in need thereof. The tumor may be carcinoma such as prostate cancer, melanoma, colon cancer, rectal cancer, liver cancer or lung cancer. The tumor may be a primary tumor. Further, the effective amount of LK8 or LK68 protein may be a dose of 0.1 to 100 mg/kg, or a dose of 1 to 50 mg/kg. The metastasis may be sinusoidal-type or portal-type, particularly in the case of colon cancer liver metastasis.

In another aspect, the invention is directed to a method for inhibiting metastasis of cancer comprising administering a combination of component (i) a composition comprising LK8 or LK68 protein or a functionally equivalent amino acid variant thereof and a pharmaceutically acceptable carrier thereof; and component (ii) radiation therapy, immunotherapy or chemotherapy to a subject in need thereof, with sufficient dosage or amount of the combination of component (i) and component (ii) to be metastasis inhibition effective. In this method, the cancer may be carcinoma such as prostate cancer, melanoma, colon cancer, rectal cancer, liver cancer or lung cancer. This method may further comprise surgery in addition to components (i) and (ii) above. Chemotherapy may include treatment with alkylating agents, antimetabolites, plant alkaloids, topoisomerase inhibitors or antitumour agents. The chemotherapy may further comprise treatment with antimetabolites. In one aspect, the antimetabolite may be 5-fluorouracil, fludarabine, or methotrexate. In another aspect, the component (ii) may include a vector which expresses LK8 or LK68.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein.

The α-factor secretion signal boundary sequence for insertion of LK8 cDNA is 5'-atg aga ttt cct tca att ttt act gca gtt tta ttc gca gca tcc tcc gca tta gct gct cca gtc aac act aca aca gaa gat gaa acg gca caa att ccg gct gaa gct gtc atc ggt tac tca gat tta gaa ggg gat ttc gat gtt gct gtt ttg cca ttt tcc aac agc aca aat aac ggg tta ttg ttt ata aat act act att gcc agc att gct gct aaa gaa gaa ggg gta tct ctc gag aaa aga-3' (SEQ ID NO:3) corresponding to the amino acid sequence Met Arg Phe Pro Ser Ile Phe Thr Ala Val Leu Phe Ala Ala Ser Ser Ala Leu Ala Ala Pro Val Asn Thr Thr Thr Glu Asp Glu Thr Ala Gln Ile Pro Ala Glu Ala Val Ile Gly Tyr Ser Asp Leu Glu Gly Asp Phe Asp Val Ala Val Leu Pro Phe Ser Asn Ser Thr Asn Asn Gly Leu Leu Phe Ile Asn Thr Thr Ile Ala Ser Ile Ala Ala Lys Glu Glu Gly Val Ser Leu Glu Lys Arg (SEQ ID NO:4).

FIGS. 2A-2B show expression and purification of recombinant human LK8 (rhLK8) protein. (A) Schematic representation of the apo(a) KV domain, which is referred to as LK8. Solid lines represent disulfide bonds. The depicted sequence of LK8 is as set forth in SEQ ID NO:2. (B) SDS-PAGE of purified rhLK8. The rhLK8 protein is indicated by an arrow. Molecular mass markers (lane M, in kilodaltons) are shown on the left.

Figure 3:
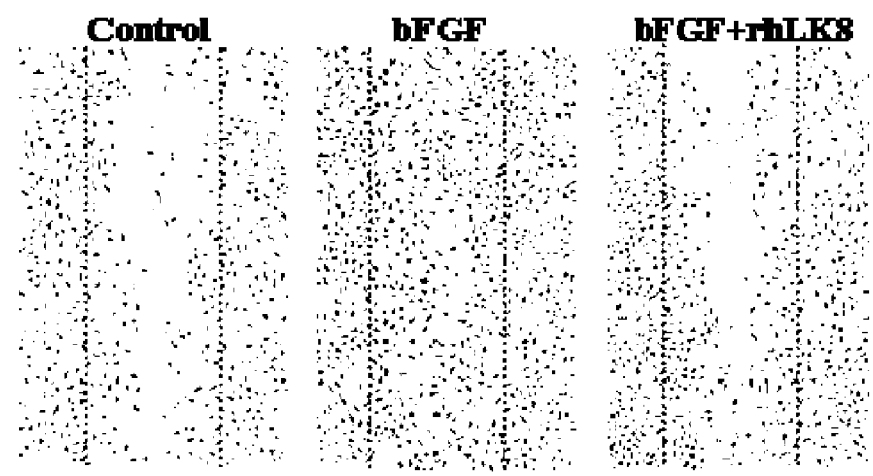
Figure 3:
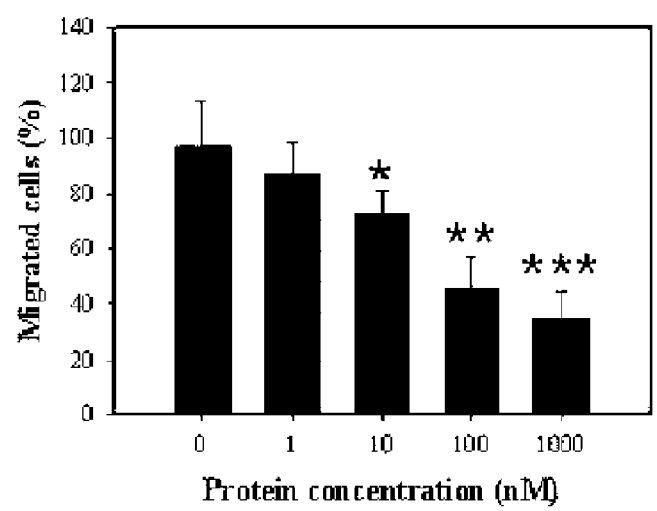

FIGS. 3A-3B show inhibition of human umbilical vein endothelial cell (HUVEC) migration by rhLK8. HUVECs were plated, scraped, and were incubated in endothelial basal medium-2 (EBM-2) supplemented with 3 ng/ml bFGF in the presence or absence of various concentrations (0.001-1 µM) of rhLK8. (A) The migration of HUVECs into the scraped area. Representative photomicrographs of untreated control cells (left) and cells treated with bFGF (center) or bFGF plus rhLK8 (right) are shown. Dotted lines indicate the area occupied by the initial scraping. (B) Quantitative measurement of cell migration. Data are expressed as percentages of the number of cells that migrated in the bFGF-treated cultures (mean±SE). The data shown are representative of three independent experiments. *, $p<0.05$; , $p<0.005$; *, $p<0.0001$ versus bFGF-treated control.

Figure 4:
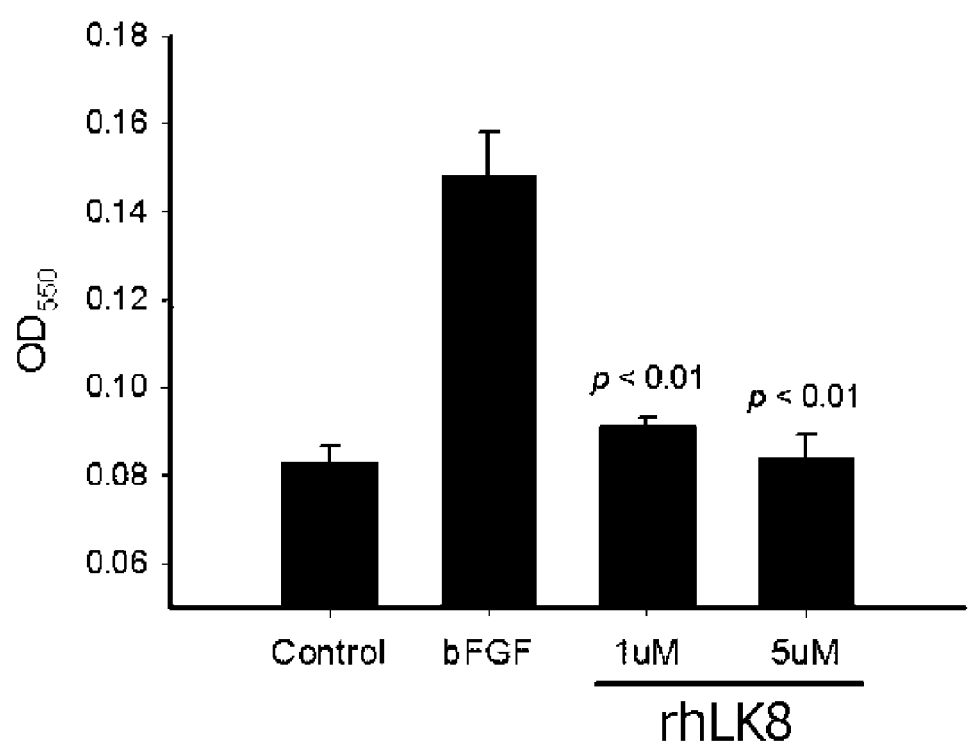

FIG. 4 shows inhibition of in vitro endothelial cell invasion through Matrigel by rhLK8. HUVECs were incubated with or without 3 ng/ml bFGF. rhLK8 protein was then added as indicated, the cells that had invaded were fixed with methanol, stained with crystal violet and extracted with 30% acetic acid, and the invasion of cells is expressed as the absorbance at 595 nm of the extracts (mean±SE).

Figure 5:
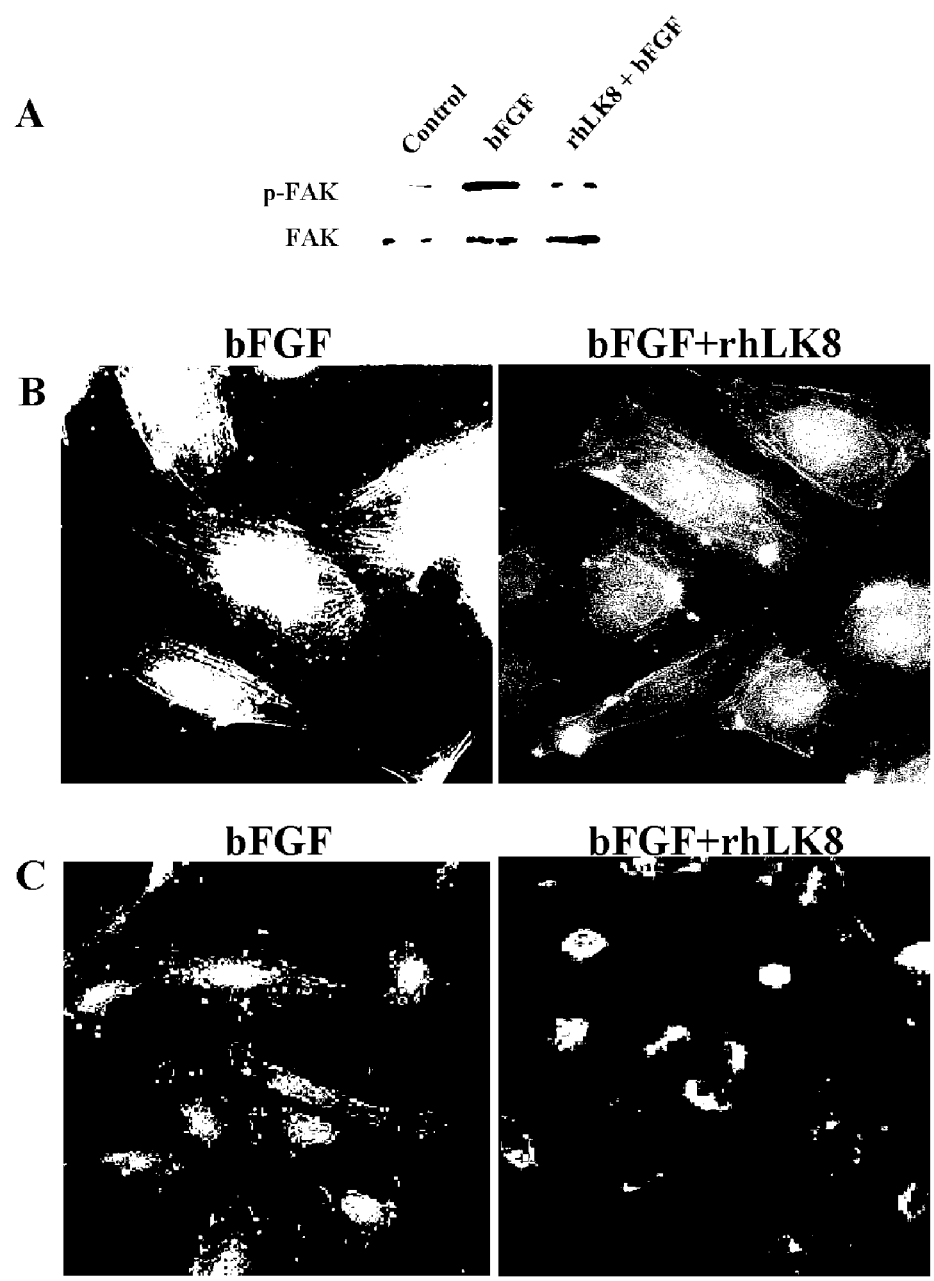

FIGS. 5A-5C show the effects of rhLK8 on focal adhesion kinase (FAK), the formation of actin stress fibers, and the formation of focal adhesions. (A) HUVECs were treated with bFGF (3 ng/ml) in the presence or absence of rhLK8 (1 µM) as indicated for 90 min at 37° C. Total cell lysate aliquots were separated by SDS-PAGE and transferred to membranes that were immunoblotted with phospho-FAK-specific antibodies (upper panel) or FAK antibodies (lower panel). The Western blot shown is representative of three independent experiments. (B and C) HUVECs cultured on coverslips were incubated for 90 min with bFGF in the presence or absence of rhLK8 (1 µM) as described. The cells were fixed and stained either with TRITC-conjugated phalloidin (B) or with antibodies against paxillin, followed by a FITC-coupled secondary antibody (C). Magnifications were ×400 (panel B) and ×200 (C).

Figure 6:
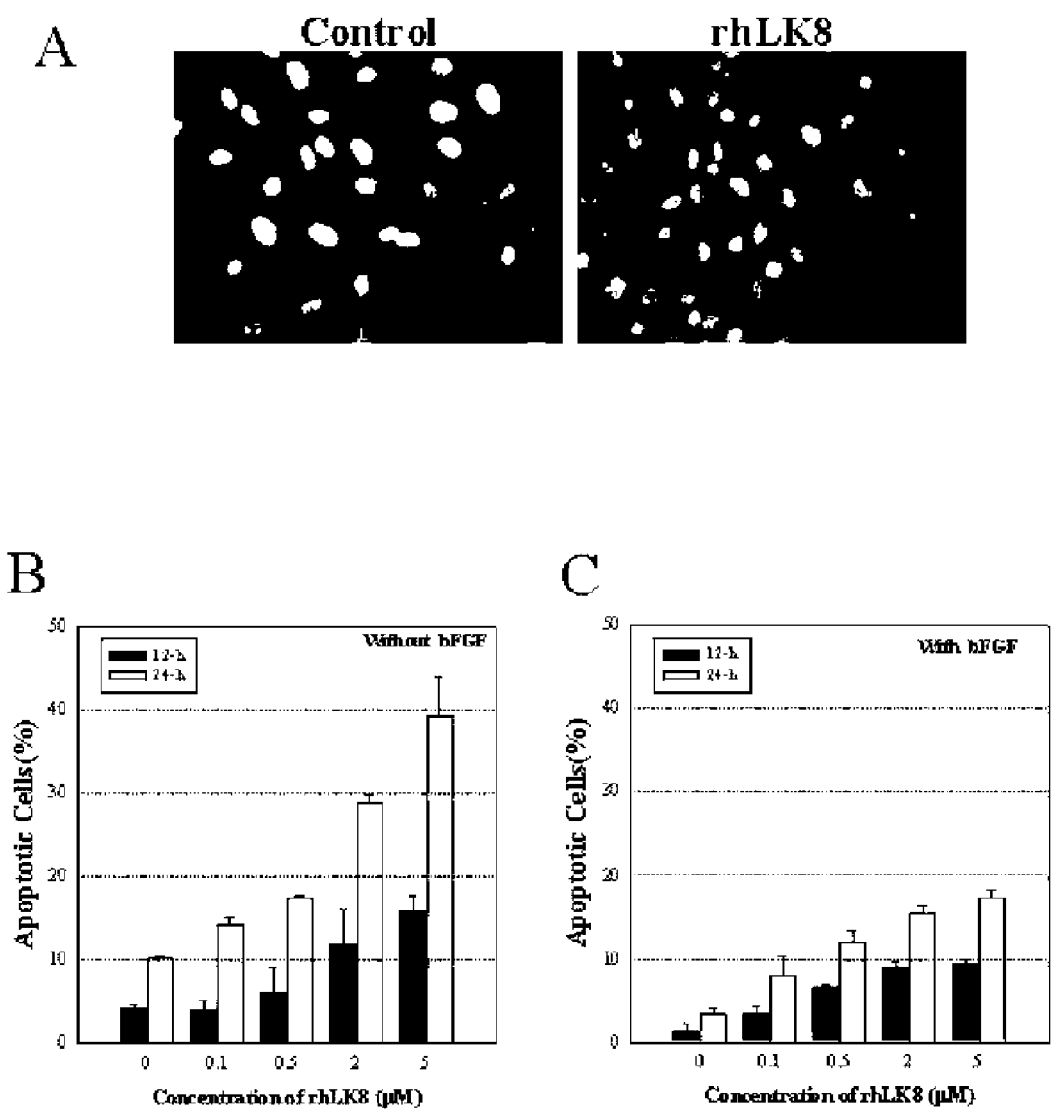

FIGS. 6A-6C show induction of endothelial cell apoptosis by rhLK8. HUVEC monolayers were incubated in EBM-2 containing 1% FBS in the presence or absence of 3 ng/ml bFGF and treated with various concentrations of rhLK8 for 12 or 24 h. Endothelial apoptosis was assessed by nuclear morphology after staining with Hoechst 33452. (A) Representative photomicrographs of HUVECs treated with PBS (left) or rhLK8 (right). (B and C) The percentage of cells undergoing apoptosis was determined in cells treated with various concentrations of rhLK8 in the absence (B) or presence (C) of bFGF after 12 (black bars) or 24 h (gray bars). Each column represents the mean±SE.

Figure 7:
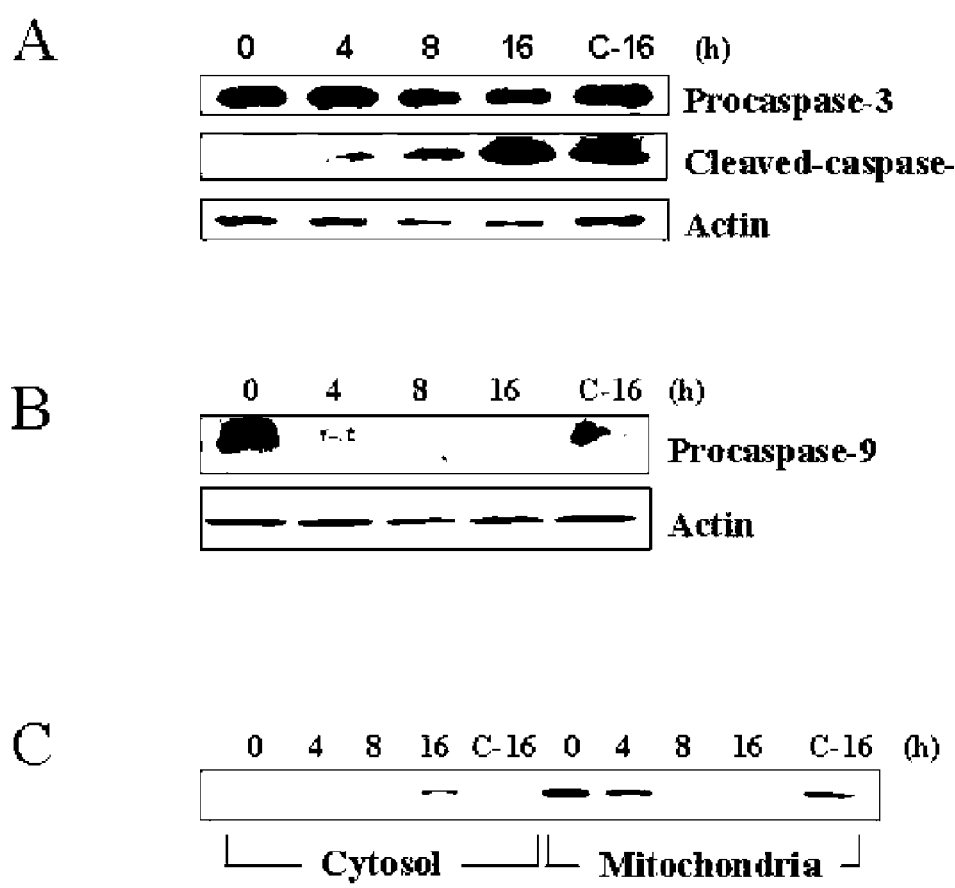

FIGS. 7A-7C show caspase activation by rhLK8 through the mitochondrial pathway. HUVECs were incubated with rhLK8 at various time points as indicated. Cells were then collected, lysed, and whole cell proteins were separated by SDS-PAGE. (A) The activation of caspase-3 was determined by Western blotting using antibodies raised against pro-caspase-3 or a 20 kDa processed form of caspase-3, as indicated. (B) Western blotting using antibodies against procaspase-9 was performed to determine the activation of caspase-9. Actin (lower panel) was used as a loading control. (C) Cytosolic and membrane-bound proteins were prepared as described (Mikhailov et al., J. Biol. Chem. 276:18361-18374, 2001) and were analyzed by Western blotting using antibodies against cytochrome C to determine the release of cytochrome C into cytosol. Protein samples loaded in the C-16 lanes were prepared from cells incubated without rhLK8 for 16 h. The immunoblots shown are the representative of at least three independent experiments.

Figure 8:
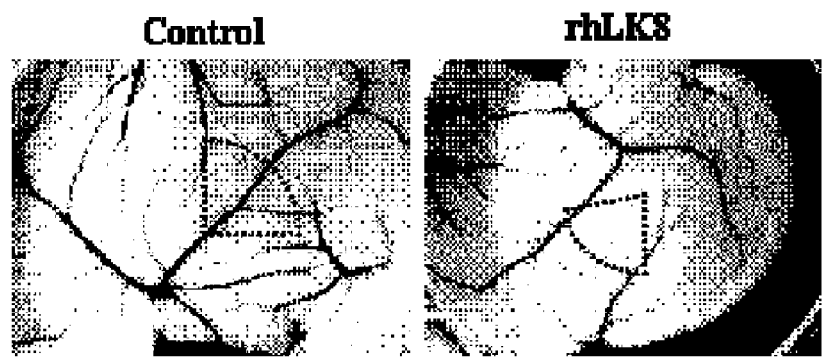
Figure 8:
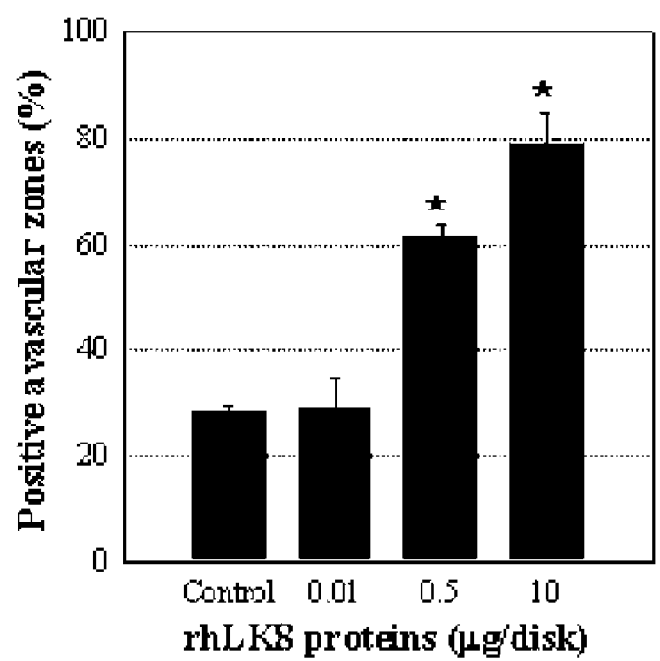

FIGS. 8A-8B show inhibition of neovascularization in the chicken chorioallantoic membrane (CAM) by rhLK8. Thermanox coverslips containing PBS or a range of concentrations of rhLK8 were applied to the CAMs of 3-day-old chick embryos. After 48 h, the formation of avascular zones (>5 mm in diameter) was analyzed. (A) Photographs of representative CAMs given Thermanox plates containing PBS (left) or rhLK8 (right). Dotted lines indicate the Thermanox plates. (B) Dose-dependent inhibition of angiogenesis in the CAM by rhLK8. Shown are the percentages of the number of CAMs showing an avascular zone relative to the total number of CAMs tested. The values are the means±SE of three independent experiments. *, $p<0.00005$.

FIGS. 9A-9F show Matrigel plug assay. (A) Sections of each Matrigel plug were stained by hematoxylin and eosin (H&E) and examined by light microscopy. The numbers of blood vessels in 4-5 high power fields were counted and averaged. Each column represents the mean±SE of the blood vessels per group. *, $p<0.005$. , $p<0.00005$. (B-F) Representative microscopic appearances of the Matrigel plugs stained with H&E (×200 magnification): B, Matrigel plug without bFGF; C, Matrigel plug with 10 ng/ml bFGF; D, E, and F, Matrigel plugs with 10 ng/ml bFGF in the presence of rhLK8 at concentrations of 50, 10, or 2 µg/ml, respectively. The insert in FIG. 9C**, shows high magnification view (×800 magnification) of a blood vessel. Its position is indicated by the dotted rectangular box.

Figure 10:
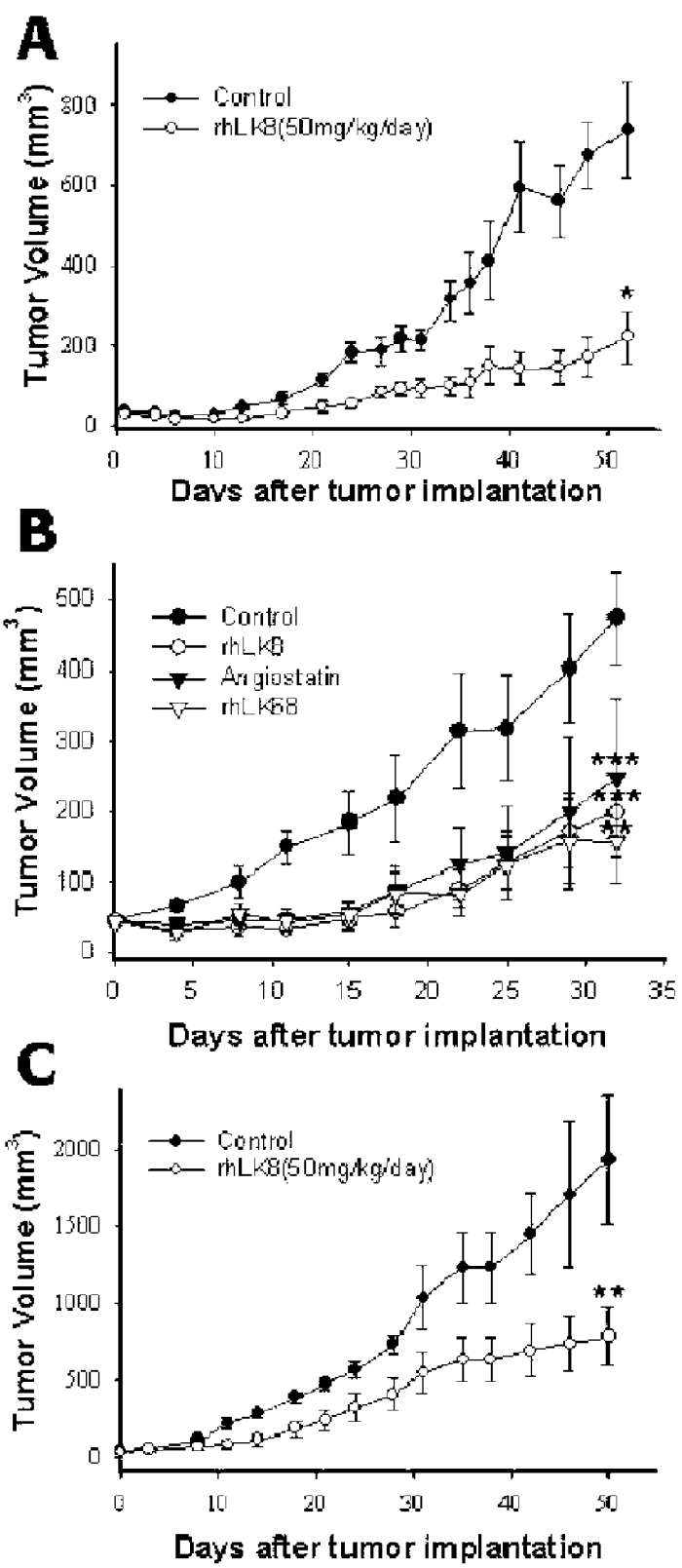
Figure 11:
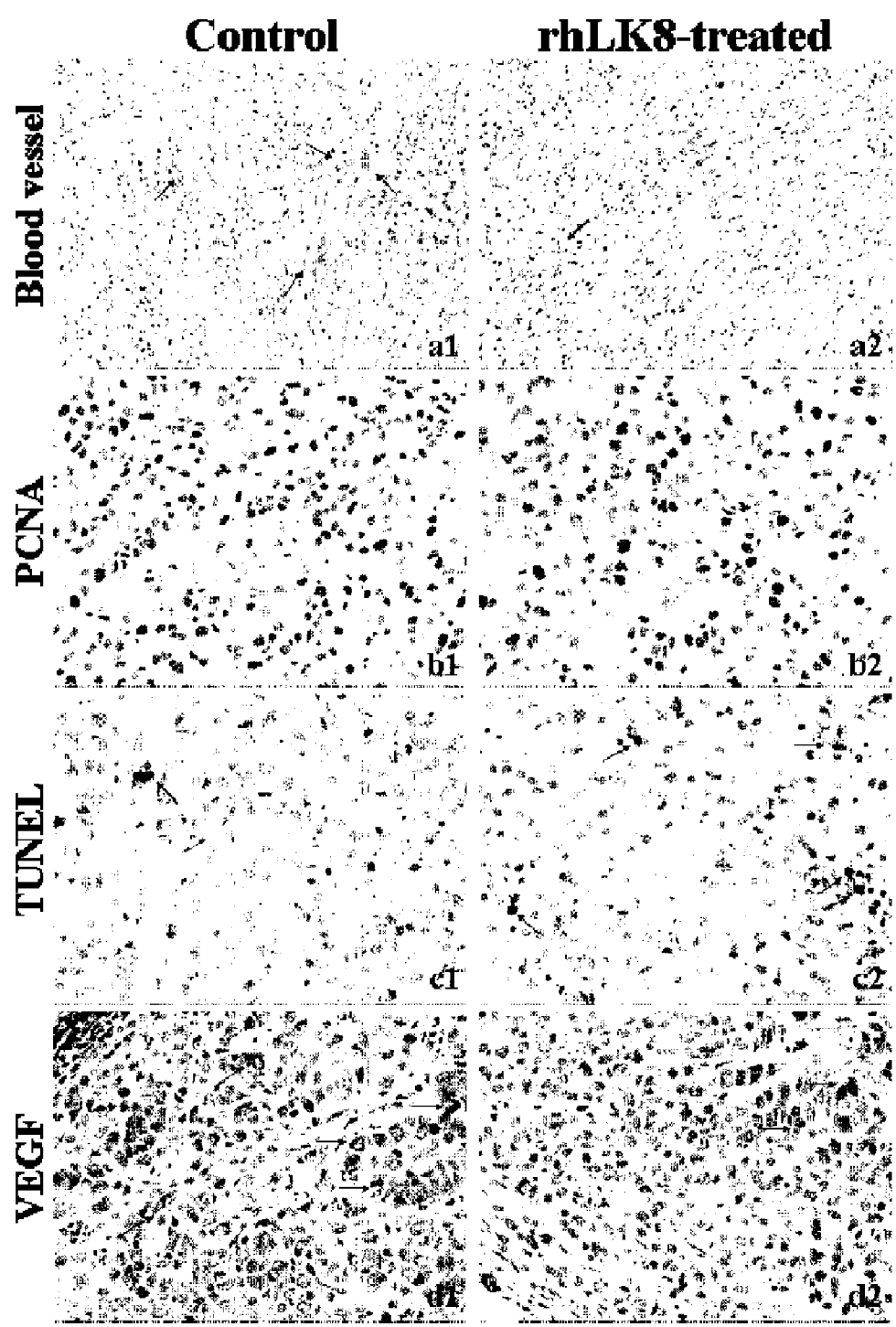
Figure 12:
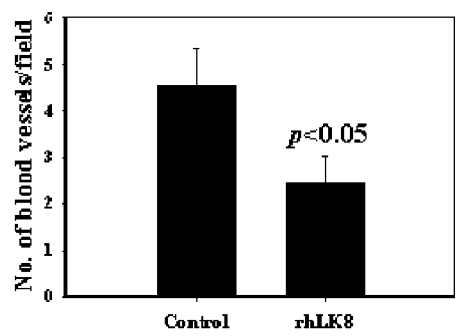
Figure 12:
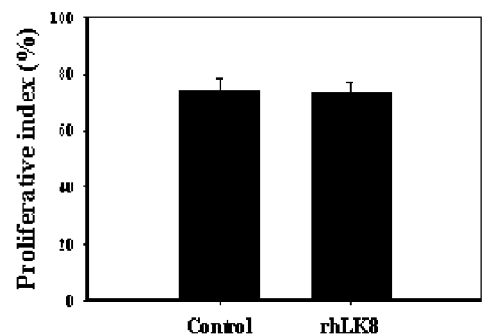
Figure 12:
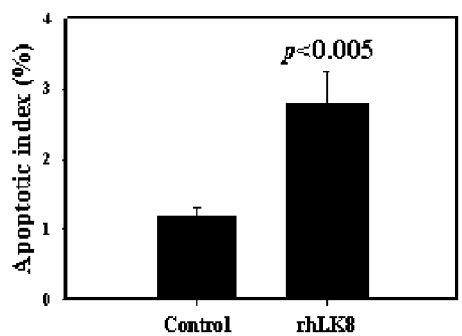
Figure 12:
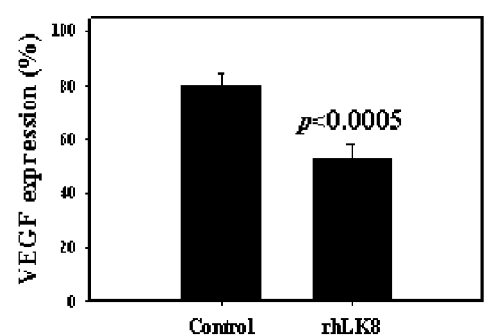

FIGS. 10A-10C show effects of rhLK8 on the growth of human tumors in nude mice. Human lung carcinoma (A549) (A and B) and human prostate carcinoma (PC-3) cells (C) were subcutaneously implanted into nude mice. The animals were then injected daily via the intraperitoneal route with rhLK8 at 100 mg/kg/day (A) or 50 mg/kg/day (B and C). Control mice were treated with PBS. In addition to rhLK8, groups of mice bearing A549 tumors were injected with (B) angiostatin or rhLK68 (both at 50 mg/kg/day) to comparatively evaluate the anti-tumor activities of those molecules. Tumor volume was calculated by the formula width$^2$×length×0.52. Each value represents the mean±SE of each group. *, $p<0.001$; , $p<0.01$; *, $p<0.05$.

FIGS. 11a1-11d2 show immunohistochemical examination of blood vessel density, proliferation, apoptosis, and vascular endothelial growth factor (VEGF) expression in rhLK8-treated and control tumors. Representative photomicrographs of tumor tissues from control (left panels) and rhLK8-treated animals (right panels) are shown. Blood vessels in control (a1) and rhLK8-treated tumors (a2) were immunostained with anti-von Willebrand factor (vWF) antibody and counted. Arrows indicate blood vessels. Magnification, ×200. (b1 and b2) Proliferating cell nuclear antigen (PCNA) immunostaining revealed extensive positive reactivity of both tumor tissues. Magnification, ×400. (c1 and c2) Apoptotic cells were detected by labeling fragmented DNA with terminal deoxynucleotidyl transferase-mediated dUTP-biotin nick end-labeling (TUNEL). Apoptotic cells are indicated by arrows. Magnification, ×400. (d1 and d2) VEGF immunostaining revealed cytoplasmic staining in tumor cells and is indicated by arrows. Magnification, ×400.

FIGS. 12A-12D show quantitative analysis of angiogenesis, proliferation, apoptosis, and VEGF expression in rhLK8-treated and control tumors. (A) The tumor tissues were immunostained with anti-vWF, and blood vessels in at least 5 random high-power fields in each animal were counted. Each column represents the mean±SE of three animals in each group. (B) Cell proliferative index was measured by counting cells stained with anti-PCNA antibody and expressed as a percentage relative to the total number of cells. (C) Apoptotic index was measured by labeling fragmented DNA in apoptotic cells using TUNEL, counting these cells and expressing these values as percentages relative to the total number of cells. (D) Histological tumor sections were stained with anti-VEGF antibodies. Positive cells were counted and these values were expressed relative to the total number of cells. (B, C, and D) Approximately 2,000 cells were counted in each animal under a magnification of ×400, and the values in each column represent the mean±SE of three or four animals.

Figure 13:
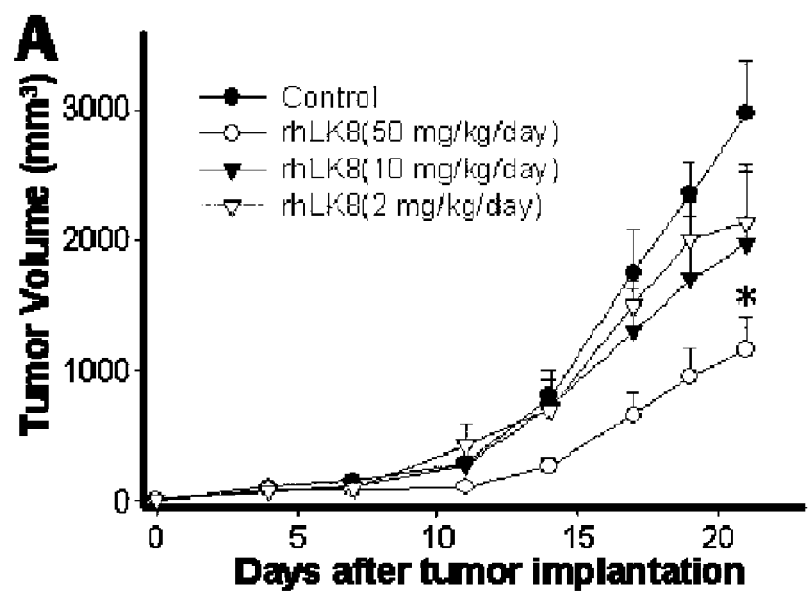
Figure 13:
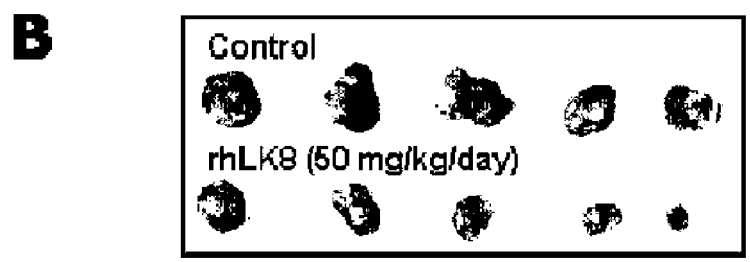
Figure 13:
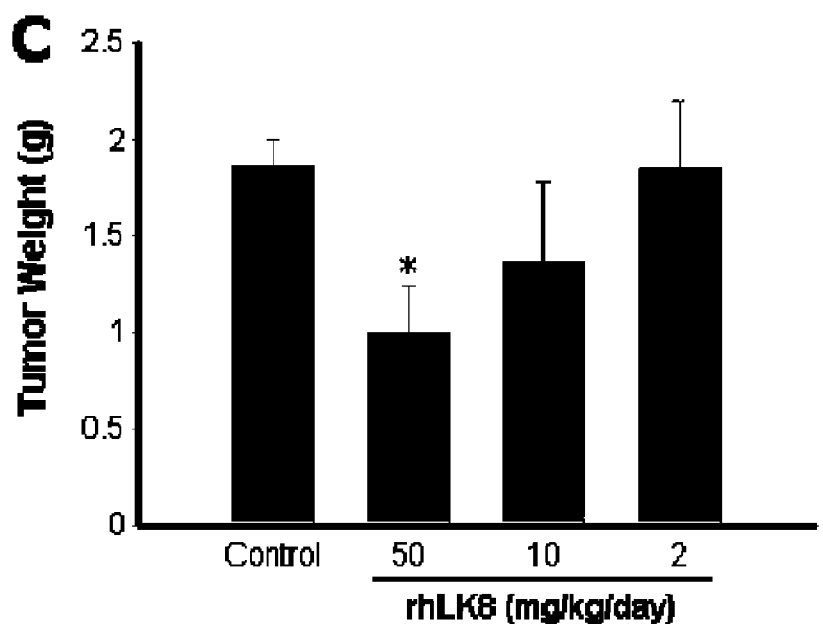

FIGS. 13A-13C show suppression of colon tumor growth by rhLK8. (A) Human colon carcinoma (LS174T) cells were subcutaneously implanted into nude mice and rhLK8 (50, 10, or 2 mg/kg/day) or PBS was injected daily via the intraperitoneal route. Tumor volume was calculated by the formula width$^2$×length×0.52. *, $p<0.01$. Each value represents the mean±SE of each group. (B) Photographs and (C) mean weights (mean±SE) of tumors collected at the time of sacrifice. *, $p<0.05$.

Figure 14:
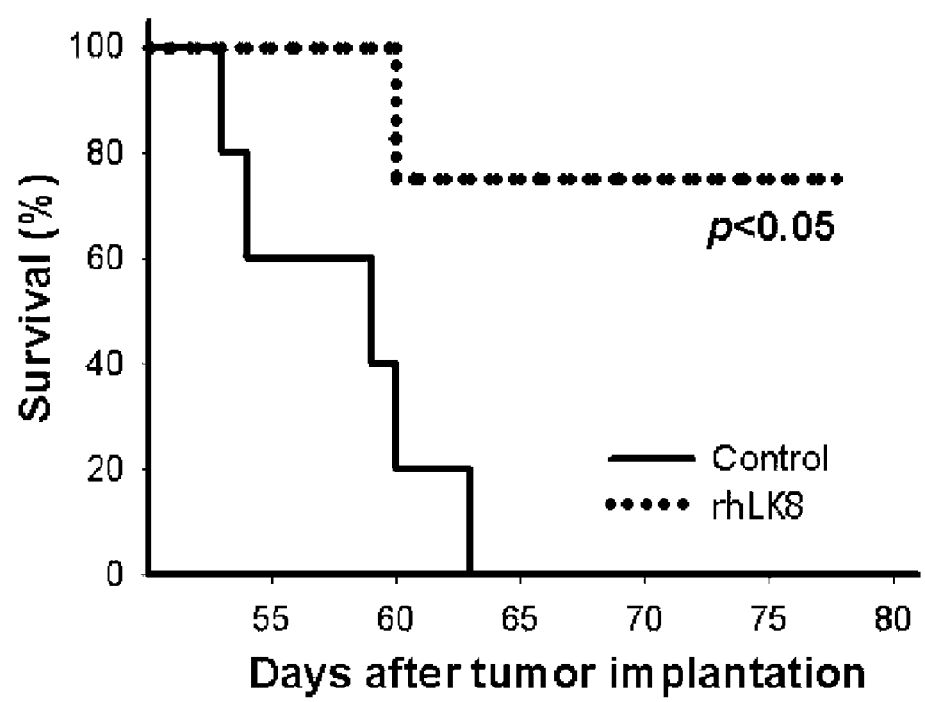
Figure 15:
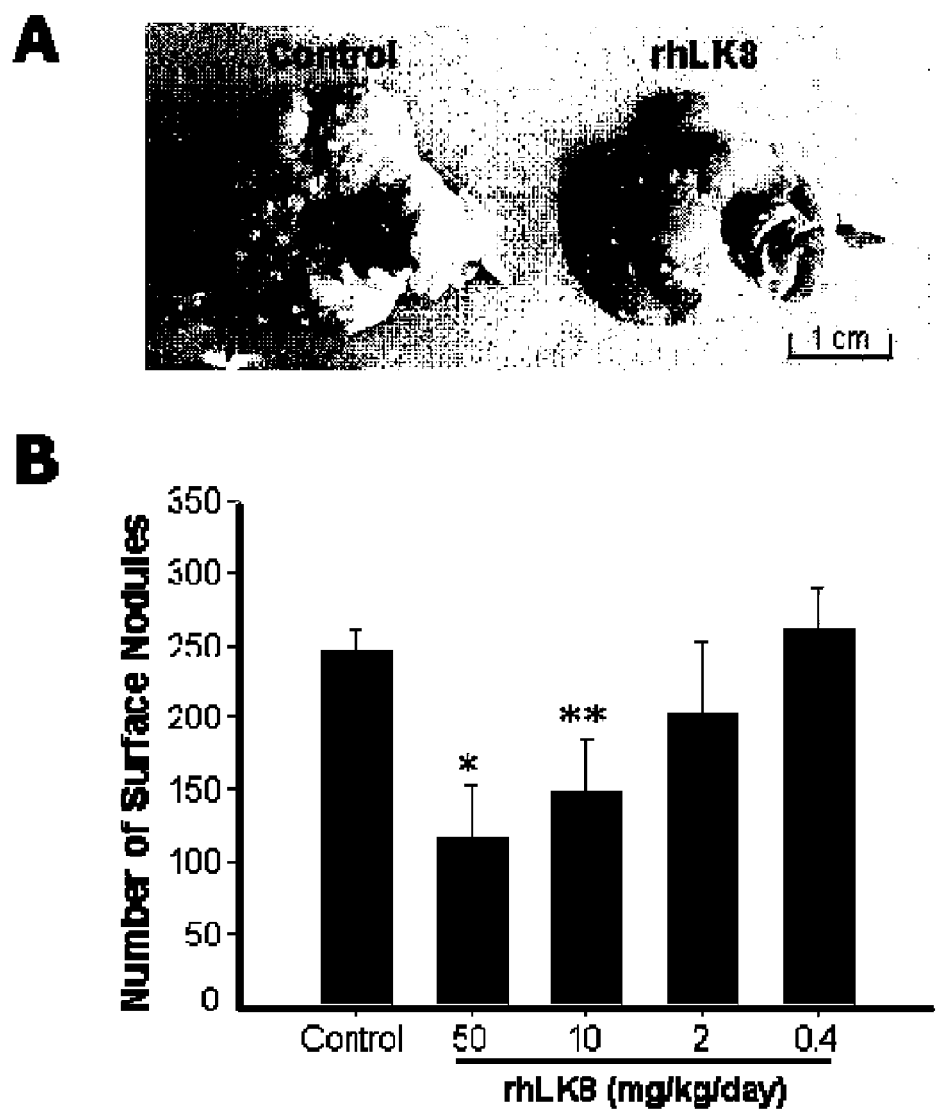
Figure 15:
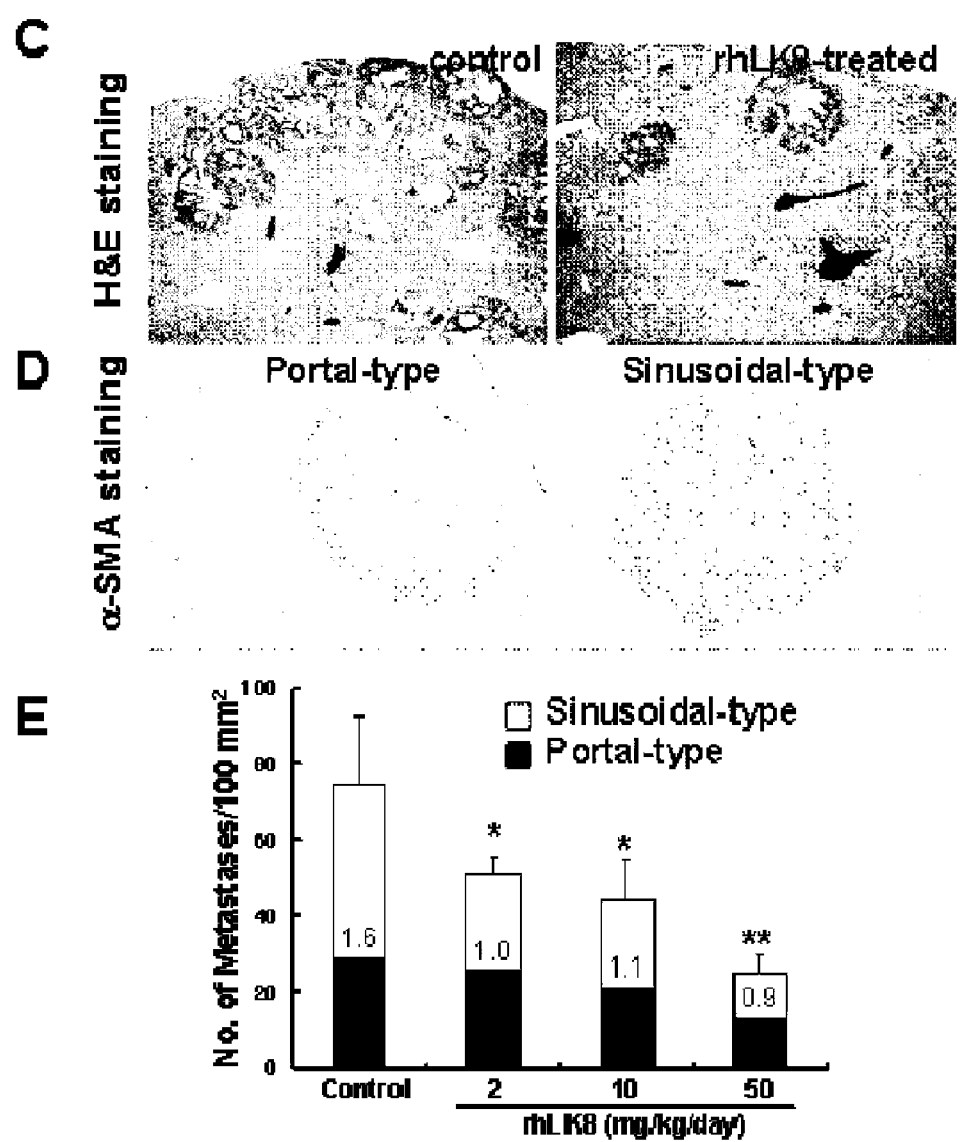

FIG. 14 shows Kaplan-Meier survival curve of mice bearing cecal tumors. Athymic BALB/c nude mice were anaesthetized intraperitoneally with Ketamin/Xylazine (100/10 mg/kg). The cecum was then exteriolized through a ventral incision and 1×10$^6$ cells of KM12SM human colorectal cancer in 30 µl of PBS were injected into the serosa of cecum using a 30-gauge needle. The peritoneum and skin were closed in two layers with metal clip. From the day of tumor inoculation, mice were administered intraperitoneally with rhLK8 (50 mg/kg/day).

FIGS. 15A-15E show suppression of colon cancer liver metastasis by rhLK8. Athymic BALB/c nude mice were anaesthetized and the spleen was then exteriolized through a left lateral flank incision. 3×10$^5$ cells of LS174T human colorectal carcinoma in 100 µl of PBS were injected into the spleen parenchyma using a 30-gauge needle. The peritoneum and skin were closed with metal clip. From the day of tumor inoculation, mice were administered intraperitoneally with rhLK8 (50, 10 or 2 mg/kg/day). Fourteen days after tumor cell implantation, mice were sacrificed and livers were collected to analyze metastasis suppression. (A) Representative photograph showing livers obtained from control (left) or rhLK8-treated (right) mice. (B) Number of surface tumor nodules in control and rhLK8-treated livers.*, $p<0.01$; **, $p<0.05$. (C) Sections of tumor tissues were stained with H&E or (D) stained with anti-α-smooth muscle actin (SMA) antibodies. Two distinct types of metastasis, sinusoidal-type and portal-type, were observed by α-SMA staining. (E) Quantitative analysis of sinusoidal and portal-type liver metastases per unit area (100 mm$^2$) of at least four randomly selected fields, showing the preferential action of rhLK8 on the sinusoidal-type metastases. The ratio of sinusoidal-type versus portal-type metastasis is shown in the bars. Differences in the number of sinusoidal-type metastasis in livers from rhLK8-treated mice versus control mice: *, $p<0.05$; **, $p<0.01$.

Figure 16:
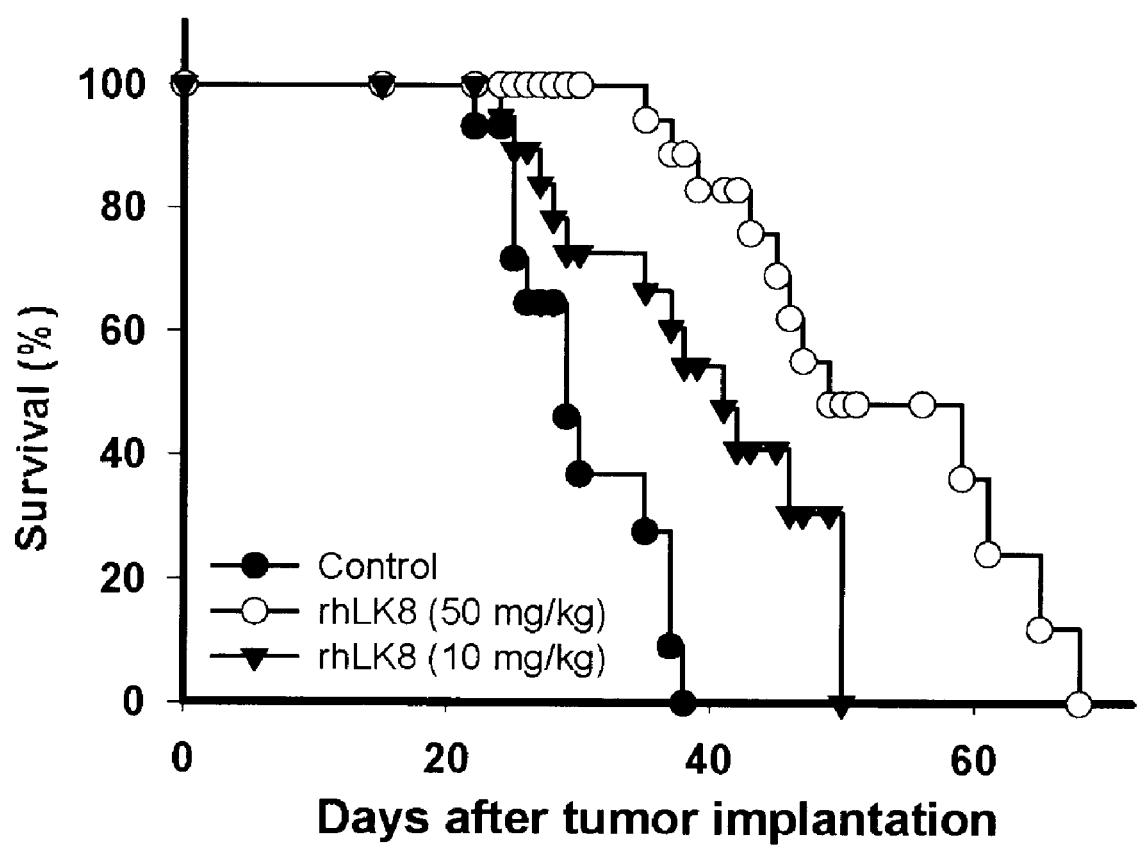

FIG. 16 shows Kaplan-Meier survival curve of mice bearing liver metastasis. Differences in survival were statistically significant, as determined by log-rank analysis. $p<0.005$, control vs. rhLK8 (10 mg/kg/day); $p<0.0001$, control vs. rhLK8 (50 mg/kg/day).

FIGS. 17A-17B show that rhLK8 inhibits experimental lung metastasis of murine melanoma cells. (A) B16-F10 murine melanoma cells ($2\times10^5$ cells) were injected into tail vein of C57BL/6 mouse, and mice were given rhLK8 (1 mg/kg) intraperitoneally from the post-operation day 0 (POD0). (A) A representative photograph after staining with Bouin's solution and (B) quantitative measurement of the surface nodules of the tumor-bearing lungs at POD14 from control and rhLK8-treated mice was shown. Lungs of the control group showed multiple tumor nodules on the surface, but number of the surface nodules in the rhLK8-treated group of mice was much lower than those of control group of mice.

Figure 18:
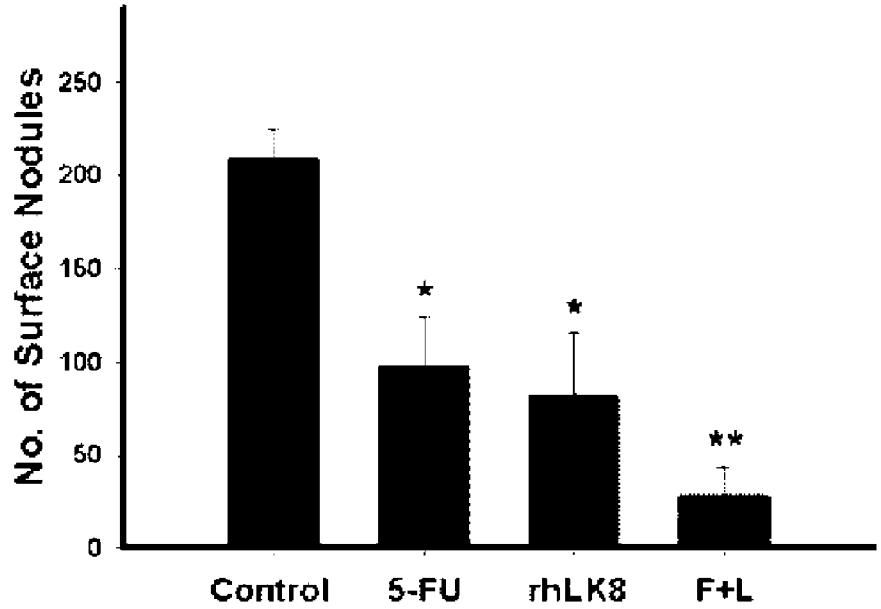
Figure 18:
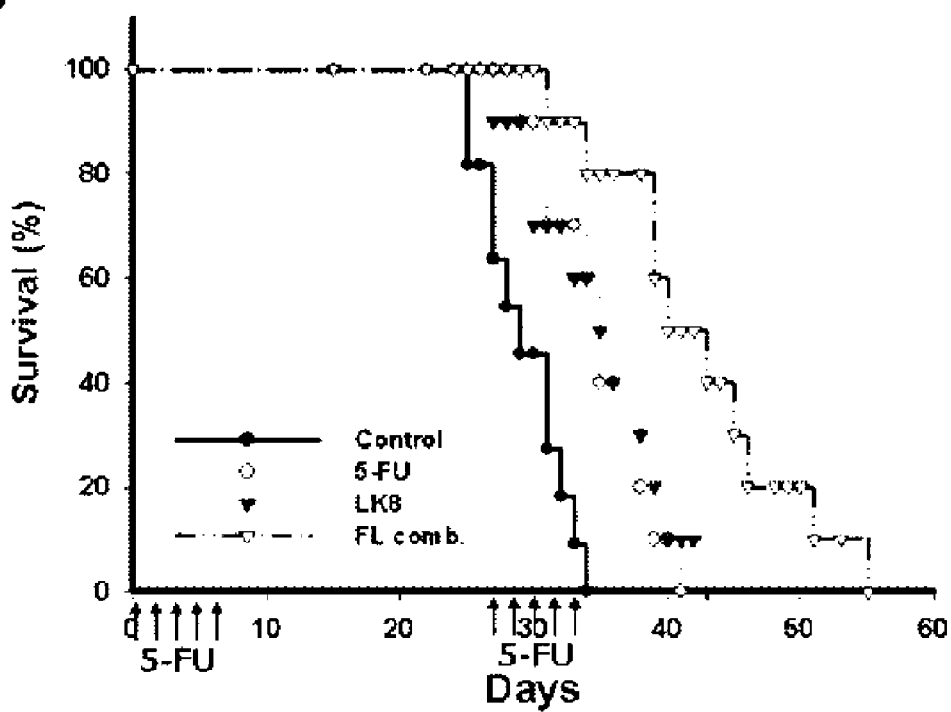

FIGS. 18A-18B show suppressive activity of rhLK8, chemotherapy with 5-FU, and combination therapy against hepatic metastasis of colorectal cancer cells. (A) Effect of treatment with rhLK8 and/or chemotherapy (5-FU) on liver metastasis of LS174T human colorectal cancer cells. Data are expressed as number of surface nodules (mean±SE). *, $p<0.05$; **, $p<0.0005$ versus control. F+L, combination therapy with rhLK8 and 5-FU. (B) Effect of treatment with rhLK8 and/or chemotherapy (5-FU) on survival of mice with liver metastasis. Kaplan-Meier survival curve of mice bearing liver metastasis was shown.

Figure 19:
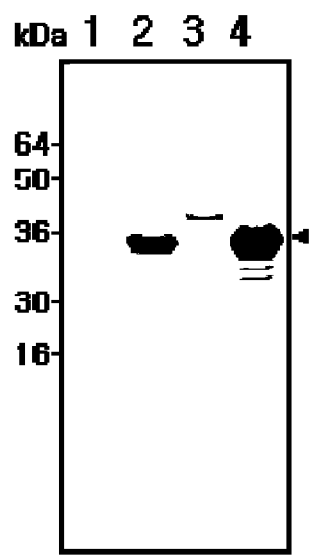
Figure 19:
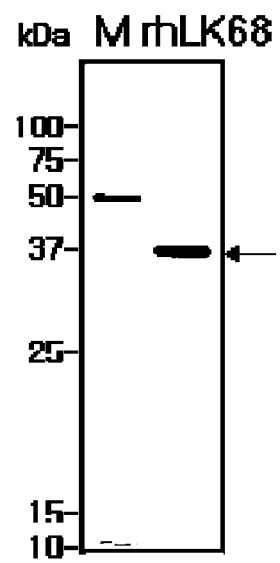

FIGS. 19A-19B show expression and purification of recombinant human LK68 (rhLK68) protein. (A) SDS-PAGE of rhLK68 expressed as an inclusion body: lane 1, uninduced bacterial lysate; lane 2, IPTG-induced bacterial lysate; lanes 3 and 4, soluble and insoluble fractions of IPTG-induced bacterial lysate, respectively. (B) SDS-PAGE of purified rhLK68. rhLK68 proteins are indicated by arrows. Molecular mass markers (in kilodaltons) are shown on the left.

FIGS. 20A-20B show suppression of primary tumor growth by rhLK68. (A) Human lung carcinoma (A549) and (B) human colon carcinoma (HCT-15) cells were subcutaneously implanted into nude mice, and rhLK68 (100 mg/kg/day) or PBS was injected daily via subcutaneous routes for 12-15 days starting from the 7th day after tumor implantation (n=5/group). Tumor volume was calculated by the formula width$^2$×length×0.52. *, $p<0.02$. Each value represents the mean±SE.

FIGS. 21a-21j show immunohistochemical observations and RNA in situ hybridization analysis of tumor tissues. Hematoxylin and eosin (H&E) staining of tumor tissues from control (a1 and a2) and rhLK68-treated mice (b1 and b2) implanted with human colon carcinoma (HCT-15) cells. Magnifications, ×100 (a1 and b1) and ×400 (a2 and b2). Immunostaining of tumor tissues using an antibody against vWF (c1 and c2), α-SMA (d1 and d2), angiogenin (e1 and e2), and VEGF (f1 and f2). RNA in situ hybridization analysis showing the mRNA expression of bFGF (g1 and g2), VEGF (h1 and h2), and vWF (i1 and i2). Each panel comprises two photomicrographs that represent tumor tissues from control (c1-i1) and rhLK68-treated (c2-i2) mice under the same magnification, ×400. Control RNA in situ hybridization of tumor tissues using sense-strand probes corresponding to bFGF (j1), VEGF (j2), and vWF (j3).

Figure 22:
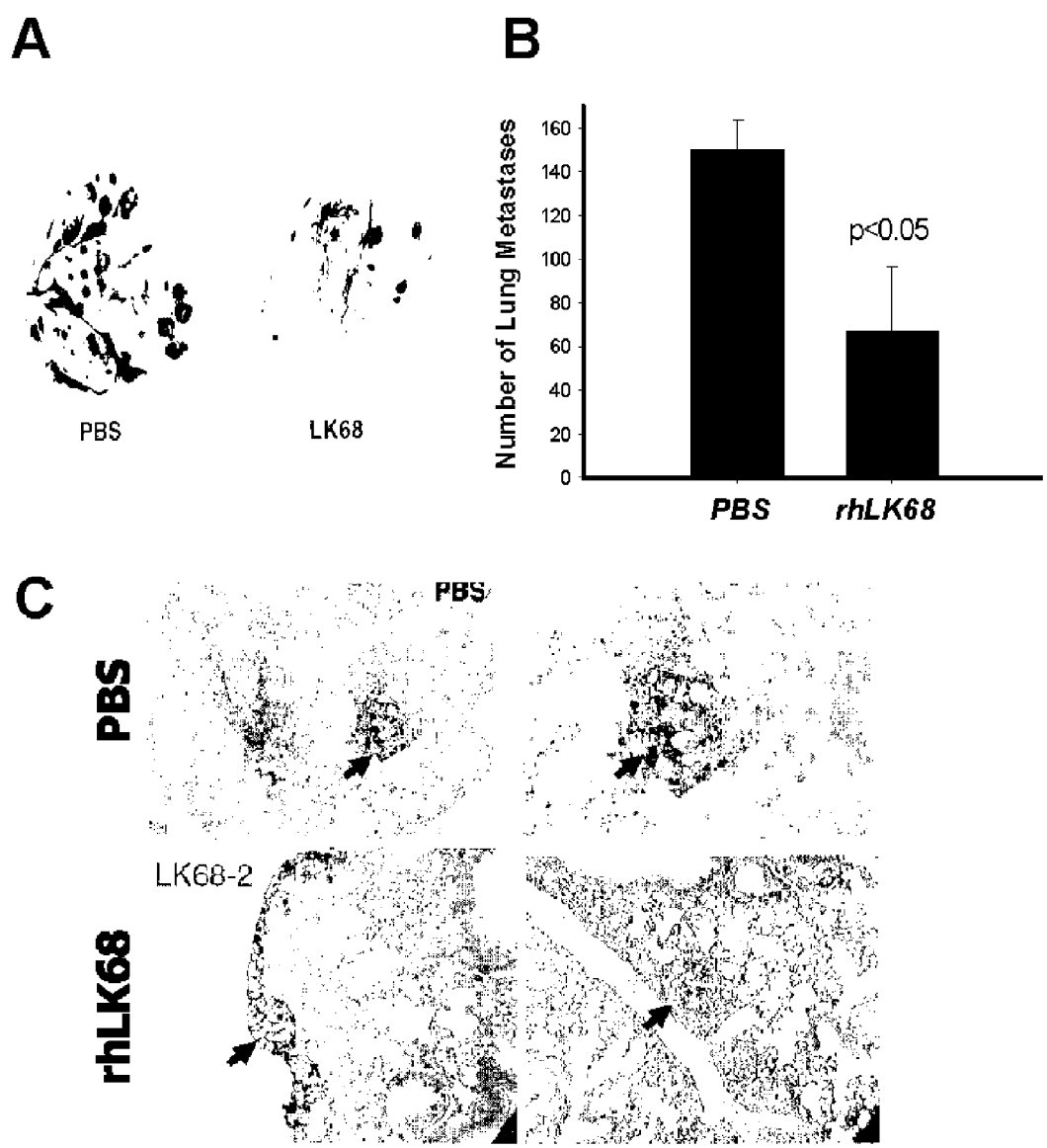

FIGS. 22A-22C show suppression of pulmonary metastasis of B16F10 melanoma cells by rhLK68. (A) Representative photograph showing lungs obtained from control (left) or rhLK68-treated (right) mice. (B) Quantitative analysis of the number of surface tumor nodules in control and rhLK68-treated lungs.*, $p<0.05$. (C) Representative photograph showing H&E-stained tissue sections of tumor-bearing lungs from control (upper panel) or rhLK68-treated (lower panel) mice.

DETAILED DESCRIPTION OF THE PREFERRED EMBODIMENTS

In the present application, "a" and "an" are used to refer to both single and a plurality of objects.

As used herein, "about" or "substantially" generally provides a leeway from being limited to an exact number. For example, as used in the context of the length of a polypeptide sequence, "about" or "substantially" indicates that the polypeptide is not to be limited to the recited number of amino acids. A few amino acids add to or subtracted from the N-terminus or C-terminus may be included so long as the functional activity such as its binding activity is present.

As used herein, administration "in combination with" one or more further therapeutic agents includes simultaneous (concurrent) and consecutive administration in any order.

As used herein, "amino acid" and "amino acids" refer to all naturally occurring L-α-amino acids. This definition is meant to include norleucine, ornithine, and homocysteine.

As used herein, in general, the term "amino acid sequence variant" refers to molecules with some differences in their amino acid sequences as compared to a reference (e.g. native sequence) polypeptide. The amino acid alterations may be substitutions, insertions, deletions or any desired combinations of such changes in a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, and so on.

Insertional variants are those with one or more amino acids inserted immediately adjacent to an amino acid at a particular position in a native amino acid sequence. Immediately adjacent to an amino acid means connected to either the α-carboxy or α-amino functional group of the amino acid.

Deletional variants are those with one or more amino acids in the native amino acid sequence removed. Ordinarily, deletional variants will have one or two amino acids deleted in a particular region of the molecule.

In one aspect, the polypeptide variants of the present invention may contain any number of amino acids or alterations of amino acids, especially in a nonfunctional region of the polypeptide, including substitutions and/or insertions and/or deletions in the region of the polypeptide molecule, so long as the polypeptide variant includes a sequence that is at least about 70%, 75%, 80%, 85%, 90%, 95%, 96%, 97%, 98% or 99% identical to the polypeptide sequence represented by SEQ ID NO:2 or SEQ ID NO:11, and the presence of the variations do not hinder the anti-angiogenesis, anti-cancer, anti-tumor or anti-metastasis effect of the polypeptide. In addition, the polypeptide may have added or subtracted from each end, N-terminus or C-terminus, about 0 to 10 amino acids, about 0 to 5, or from 0 to 4 or from about 0 to 3 or from 0 to 2 or from 0 to 1 amino acids from the polypeptide of SEQ ID NO:2 or SEQ ID NO:11.

As used herein, "carriers" include pharmaceutically acceptable carriers, excipients, or stabilizers which are non-toxic to the cell or mammal being exposed thereto at the dosages and concentrations employed. Often the pharmaceutically acceptable carrier is an aqueous pH buffered solution. Examples of pharmaceutically acceptable carriers include without limitation buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

As used herein, "effective amount" is an amount sufficient to effect beneficial or desired clinical or biochemical results. An effective amount can be administered one or more times. For purposes of this invention, an effective amount of an inhibitor compound is an amount that is sufficient to palliate, ameliorate, stabilize, reverse, slow or delay the progression of the disease state. In a preferred embodiment of the invention, the "effective amount" may be that amount of LK8 or LK68 that is able to inhibit angiogenesis in vivo, which inhibits formation of new blood vessels and thus inhibits the growth of tumors.

A composition is said to be "pharmacologically or physiologically acceptable" if its administration can be tolerated by a recipient animal and is otherwise suitable for administration to that animal. Such an agent is said to be administered in a "therapeutically effective amount" if the amount administered is physiologically significant. An agent is physiologically significant if its presence results in a detectable change in the physiology of a recipient patient.

As used herein, "sequence identity", is defined as the percentage of amino acid residues in a candidate sequence that are identical with the amino acid residues in a native polypeptide sequence after aligning the sequences and introducing gaps, if necessary, to achieve the maximum percent sequence identity, and not considering any conservative substitutions as part of the sequence identity. The % sequence identity values are generated by the NCBI BLAST2.0 software as defined by Altschul et al., (1997), "Gapped BLAST and PSI-BLAST: a new generation of protein database search programs", Nucleic Acids Res., 25:3389-3402. The parameters are set to default values, with the exception of the Penalty for mismatch, which is set to −1.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" refers to both therapeutic treatment and prophylactic or preventative measures. Those in need of treatment include those already with the disorder as well as those in which the disorder is to be prevented. "Palliating" a disease means that the extent and/or undesirable clinical manifestations of a disease state are lessened and/or the time course of the progression is slowed or lengthened, as compared to a situation without treatment.

The anticancer agent of the present invention is characterized by including LK8 or LK68 protein having an amino acid sequence represented by SEQ ID NO:2 or SEQ ID NO:11, respectively, or a functionally equivalent amino acid variant thereof as an active ingredient. It is understood that mutations to the LK8 or LK68 sequence and/or the addition or deletion of amino acids from the N- or C-terminus of the LK8 or LK68 that do not alter the tumor growth inhibiting property or metastasis inhibiting property of these polypeptide molecules is fully encompassed by the invention.

In one embodiment, the invention is directed to a metastasis inhibitor, more preferably, is the agent may be used for the suppression of metastasis of a variety of tumors including without limitation from any tumor origin to another organ, in particular, colon carcinoma or rectal cancer to liver, and melanoma to lung.

In addition, in another embodiment, the anticancer agent may be used for the treatment of primary tumors. More preferably, the agent is used for the treatment of a cancer including without limitation carcinoma, melanoma and sarcoma. Subtypes of cancer may include without limitation bladder carcinoma, brain tumor, breast cancer, cervical cancer, colorectal cancer, esophageal cancer, endometrial cancer, hepatocellular carcinoma, gastrointestinal stromal tumor (GIST), laryngeal cancer, lung cancer, osteosarcoma, ovarian cancer, pancreatic cancer, prostate cancer, renal cell carcinoma or thyroid cancer. In particular, the cancer may be selected from the group consisting of prostate cancer, lung cancer, colon cancer and rectal cancer.

It is preferred for the anticancer agent of the present invention to contain LK8 protein by 0.1~100 mg/kg, more preferred to contain LK8 protein by 1~50 mg/kg, and administration times may be 1~4 per day. But the composition is not limited thereto, and is possibly changed according to the conditions of a patient, and types and rate of progression of the disease.

LK8 and LK68

In this invention, "KIV36" means Apo(a) kringle IV (subtype 9; also referred to as KIV9); "KIV37" means Apo(a) kringle IV (subtype 10; also referred to as KIV10); and "KV38" means Apo(a) kringle V (also referred to as KV). "LK8" means a recombinant protein of KV38 and "LK68" means a recombinant protein of KIV36-KIV37-KV38. However, both KV38 and LK8 protein may be used to refer to LK8 protein in general unless mentioned specifically. Similarly, both KIV36-KIV37-KV38 and LK68 protein may be used to refer to LK68 protein in general unless mentioned specifically.

LK8 and LK68 proteins of the present invention have an inhibitory effect on proliferation and differentiation of cancer cells and metastasis by suppressing the activity of endothelial cells in vitro and in vivo. As explained in the preferred embodiment of the present invention, the systemic administration of LK8 protein results in the inhibition of a primary tumor and its metastasis (see FIG. 10~FIG. 18). LK68 protein of the present invention has an anti-angiogenic activity both in vitro and in vivo and suppresses primary tumor growth and its metastasis (see FIG. 20~FIG. 22). Therefore, the LK8 or LK68 protein of the present invention can be effectively used as an anticancer agent especially for inhibiting primary tumor growth and as a metastasis inhibitor owing to its functions of suppressing tumor growth and metastasis.

As practiced, the invention is not limited to the use of the exemplified exact 86 amino acid sequence polypeptide as represented in SEQ ID NO:2 or the 308 amino acid sequence polypeptide as represented in SEQ ID NO:11. Rather, the invention encompasses certain amino acid variations that may be made to the polypeptide of SEQ ID NO:2 or SEQ ID NO:11 such that the variant polypeptide accomplishes substantially the same effect as the exemplified polypeptide of SEQ ID NO:2 or SEQ ID NO:11 in anti-angiogenesis, anti-tumor, anti-cancer and/or anti-metastasis activities. In this regard, the functionally equivalent amino acid variant of the exemplified LK8 or LK68 polypeptide may be at least about 70%, 75%, 80%, 85%, 90%, 95%, 96%, 97%, 98%, or 99% identical to the polypeptide sequence represented by SEQ ID NO:2 or SEQ ID NO:11, respectively.

In another aspect of the invention, the treatment effect may be enhanced when LK8 or LK68 protein of the present invention is used together with chemotherapy or radiotherapy. Radiotherapy is performed to destroy a primary tumor, and if LK8 or LK68 protein is administered during radiotherapy, metastasis can be prevented more effectively. As for chemotherapy, cytotoxicity caused by huge dosage of chemical anticancer agents is the biggest problem. If LK8 or LK68 protein of the invention is administered during chemotherapy, usage of even small amount of chemical anticancer agents will have anti-cancer effect or even greater anticancer effect while causing little cytotoxicity, Combination therapy, which includes administration of LK8 or LK68 protein together with surgical operation, radiotherapy, chemotherapy or immunotherapy, results in an improved effect over using the surgical operation, radiotherapy, chemotherapy or immunotherapy treatment alone. And further, the continuous administration of LK8 or LK68 protein extends dormancy of micrometastasis, suppresses the growth of a primary tumor and stabilizes conditions. Moreover, anti-angiogenic anti-cancer therapy requires the long-term administration of relatively high concentrations of recombinant proteins to ensure tumor growth suppression in vivo. Long-term systemic delivery of recombinant molecules is an expensive and painstaking process for the patient, and may be difficult to maintain prolonged high concentrations of therapeutic protein in the tumor mass. Anti-angiogenic gene therapy is an attractive solution due to the production of high concentrations of therapeutic agents in a local area for a sustained period. Systemic or local delivery of the gene encoding LK8 or LK68, either alone or in combination with the surgical operation, radiotherapy, chemotherapy or immunotherapy, to optimize the suppression of the angiogenesis-dependent growth of a variety of tumors and their metastasis is also contemplated within the framework of the invention.

Formulation

The anticancer agent comprising LK8 or LK68 protein of the present invention can be administered orally or parenterally and may be used in a pharmaceutically acceptable formulation.

The anticancer agent can be prepared for oral or parenteral administration by mixing with generally used fillers, extenders, binders, wetting agents, disintegrating agents, diluents such as surfactants, or excipients. Solid formulations for oral administration may include tablets, pills, dusting powders, granules and capsules. These solid formulations may be prepared by mixing one or more suitable excipients such as starch, calcium carbonate, sucrose or lactose, gelatin, etc. Except for the simple excipients, lubricants such as magnesium stearate, talc, and so forth, can be used. Liquid formulations for oral administration may include suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, and suppositories. Water insoluble excipients and suspensions can contain, in addition to the active compound or compounds, propylene glycol, polyethylene glycol, vegetable oil such as olive oil, injectable ester such as ethylolate, and so forth. Suppositories can contain, in addition to the active compound or compounds, witepsol, macrogol, tween 61, cacao butter, laurin butter, glycerinated gelatin, and so on.

LD50 of the LK8 protein is about 1,000 mg/kg, suggesting that the anticancer agent of the present invention is considered to be safe (see Table 2).

The present invention is directed to treating a variety of cancers, including without limitation carcinoma, melanoma and sarcoma. Subtypes of cancer may include without limitation bladder carcinoma, brain tumor, breast cancer, cervical cancer, colorectal cancer, esophageal cancer, endometrial cancer, hepatocellular carcinoma, gastrointestinal stromal tumor (GIST), laryngeal cancer, lung cancer, osteosarcoma, ovarian cancer, pancreatic cancer, prostate cancer, renal cell carcinoma or thyroid cancer.

Chemotherapy

Chemotherapeutic drugs can be divided into alkylating agents, antimetabolites, plant alkaloids, topoisomerase inhibitors, and antitumor agents. All of these drugs affect cell division or DNA synthesis and function in some way. Some agents do not directly interfere with DNA such as tyrosine kinase inhibitor (Gleevec®).

Alkylating Agents

Alkylating agents are so named because of their ability to add alkyl groups to many electronegative groups under conditions present in cells. They stop tumor growth by cross-linking guanine nucleobases in DNA double-helix strands. Examples include cisplatin, carboplatin, ifosfamide, chlorambucil, busulfan, thiotepa.

Anti-Metabolites

Anti-metabolites mimic purine or pyrimidine and prevent these substances from becoming incorporated in to DNA during replication. Examples include 5-fluorouracil (5FU), which inhibits thymidylate synthase; fludarabine, which inhibits function of multiple DNA polymerases, DNA primase and DNA ligase I; and methotrexate, which inhibits dihydrofolate reductase, an enzyme essential for purine and pyrimidine synthesis.

Plant Alkaloids

These alkaloids are derived from plants and block cell division by preventing microtubule function. Microtubules are vital for cell division and without them it can not occur. The main examples are vinca alkaloids and taxanes.

Vinca Alkaloids

Vinca alkaloids bind to specific sites on tubulin, inhibiting the assembly of tubulin into microtubules. They are derived from the Madagascar periwinkle, *Catharanthus roseus* (formerly known as *Vinca rosea*).

Taxanes

Taxanes are derived from the Pacific yew tree, Taxus brevifolia. Taxanes enhance stability of microtubules, preventing the separation of chromosomes during anaphase.

Topoisomerase Inhibitors

Topoisomerases are essential enzymes that maintain the topology of DNA. Inhibition of type I or type II topoisomerases interferes with both transcription and replication of DNA by upsetting proper DNA supercoiling. Some type I topoisomerase inhibitors include camptothecins: irinotecan and topotecan. Examples of type II inhibitors include amsacrine, etoposide, etoposide phosphate, and teniposide. The latter are semisynthetic derivatives of epipodophyllotoxins, alkaloids naturally occurring in the root of mayapple (*Podophyllum peltatum*).

Antitumor Antibiotics

There are many differing antitumor antibiotics, but generally they prevent cell division by several ways: (1) binding to DNA through intercalation between two adjacent nucleotide bases and making it unable to separate, (2) inhibiting ribonucleic acid (RNA), preventing enzyme synthesis, (3) interfering with cell replication. They are products of various strains of the soil fungus *Streptomyces*. Examples are anthracyclines (doxorubicin, daunorubicin and epirubicin, which also inhibit topoisomerase II), actinomycin, bleomycin, mitomycin and plicamycin. Bleomycin acts in unique way through oxidation of a DNA-bleomycin-Fe(II) complex and forming free radicals, which induce damage and chromosomal aberrations.

Gene Therapy

In a specific embodiment, nucleic acids comprising sequence encoding LK8 or LK68 protein are administered together with LK8 or LK68 protein itself to treat cancer. Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11 (5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors, or by direct injection of naked DNA, or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432, 1987) (which can be used to target cell types specifically expressing the receptors) and so on. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor. Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijistra et al., Nature 342:435-438 (1989)).

In a specific embodiment, viral vectors that contain nucleic acid sequences encoding the polypeptide are used. The nucleic acid sequences encoding the polypeptide to be used in gene therapy are cloned into one or more vectors, which facilitates delivery of the gene into a patient. Retroviral vectors, adenoviral vectors and adeno-associated viruses are examples of viral vectors that may be used. Retroviral vectors contain the components necessary for the correct packaging of the viral genome and integration into the host cell DNA.

Adenoviruses are especially attractive vehicles for delivering genes to respiratory epithelia because they naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. In addition, adeno-associated virus (AAV) has also been proposed for use in gene therapy.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion and so on. Numerous techniques are known in the art for the introduction of foreign genes into cells and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T-lymphocytes, B-lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, and so on.

Angiogenesis Inhibitors to Treat Angiogenesis-Related Diseases

Angiogenesis inhibitors such as LK8 and LK68 protein may be effective in treating diseases or processes that are mediated by, or involve, angiogenesis. The present invention includes the method of treating an angiogenesis-mediated disease with an effective amount of LK8 or LK68, alone or in combination with other conventional treatment modalities. The angiogenesis-mediated diseases include, but are not limited to, solid tumors; blood-born tumors such as leukemias; tumor metastasis; benign tumors such as hemangiomas, trachomas, acoustic neuromas, neurofibromas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasias, rubeosis; Osler-Webber Syndrome; myocardial angiogenesis; plaque neovascularization; telangiectasia; hemophilic joints; angiofibroma; and wound granulation (Folkman, J., N. Eng. J. Med. 333:1757-1763, 1995; Folkman, J., Nat. Med. 1:27-31, 1995). LK8 or LK68, including functionally equivalent amino acid variants or biologically active fragments thereof, is useful in the treatment of disease of excessive or abnormal stimulation of endothelial cells. These diseases include, but are not limited to, intestinal adhesion, Crohn's disease, atherosclerosis, scleroderma, and hypertrophic scars, i.e., keloids. LK8 or LK68 is useful in the treatment of diseases that have angiogenesis as a pathologic consequence such as cat scratch disease (*Rochele minalia quintosa*) and ulcers (*Helicobacter pylori*). Angiogenesis may contribute to excess accumulation of body fat in obese individuals. Indeed, preadipocytes migrate to sites of neovascularization and adipose tissue is highly angiogenic (Silverman, K. J. et al., Biochem. Biophys. Res. Commun. 153:347-352, 1988). VEGF, bFGF (induced by insulin) and leptin (a central mediator in obesity) have been identified as mediators of angiogenesis in adipose tissue. In this context, LK8 or LK68 is useful to treat obese patients.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1

Expression of Recombinant Human LK8 (rhLK8) in *Pichia pastoris*

Example 1.1

Construction of a Vector that Expresses LK8 Named pMBRI-LK8

Figure 1:
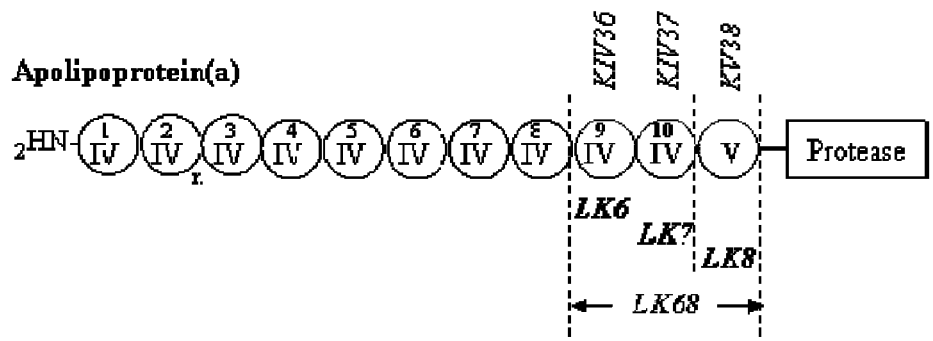
FIGS. 1A-1B show schematic representation of Apolipoprotein (a) kringle domains and expression vector construction. (A) Apo(a) contains 10 unique kringle IV-like domains designated "IV-1" through "IV-10"; kringle IV-2 is variably repeated as indicated by subscript n. One kringle V-like domain (KV) and a protease domain aligned with LK6, LK7, LK8, or LK68 are also present. (B) The expression vector 'MBRI-LK8 (8.25 kb)', in which LK8 cDNA (261 bp) is inserted between AOX1 promoter and AOX1 terminator. The sequence of the LK8 cDNA is as follows: 5'-gaa caa gac tgt atg ttt ggg aat ggg aaa gga tac cgg ggc aag aag gca acc act gtt act ggg acg cca tgc cag gaa tgg gct gcc cag gag ccc cat aga cac agc acg ttc att cca ggg aca aat aaa tgg gca ggt ctg gaa aaa aat tac tgc cgt aac cct gat ggt gac atc aat ggt ccc tgg tgc tac aca atg aat cca aga aaa ctt ttt gac tac tgt gat atc cct ctc tgt gca tcc tct taa (stop codon)-3' (SEQ ID NO:1), which corresponds to the amino acid sequence Glu Gln Asp Cys Met Phe Gly Asn Gly Lys Gly Tyr Arg Gly Lys Lys Ala Thr Thr Val Thr Gly Thr Pro Cys Gln Glu Trp Ala Ala Gln Glu Pro His Arg His Ser Thr Phe Ile Pro Gly Thr Asn Lys Trp Ala Gly Leu Glu Lys Asn Tyr Cys Arg Asn Pro Asp Gly Asp Ile Asn Gly Pro Trp Cys Tyr Thr Met Asn Pro Arg Lys Leu Phe Asp Tyr Cys Asp Ile Pro Leu Cys Ala Ser Ser (SEQ ID NO:2).
Figure 1:
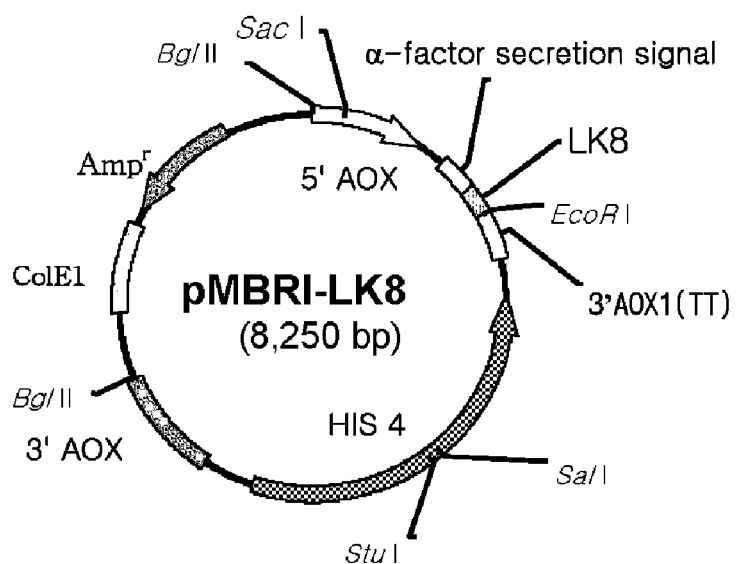
Figure 1:
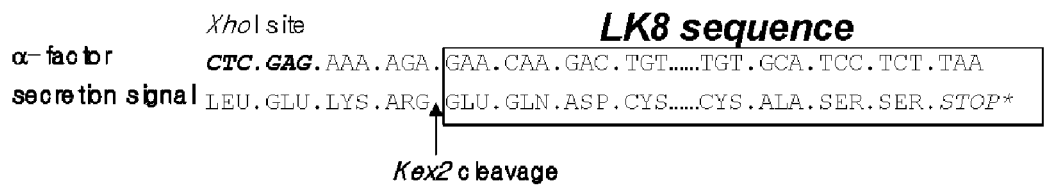

The cDNA sequence encoding LK8 was amplified by PCR that used a human liver cDNA library as a template and the primers LK8N-XhoI (5'-TCCGCTCGAGAAAA-GAGAACAAGACTGTATGTTT-3' (SEQ ID NO:5)) and LK8C-BamHI (5'-CGAATTCTTAAGAGGATGCACA-GAGAGGGAT-3' (SEQ ID NO:6)). These primers were designed to amplify the fragment between nucleotides 12,718 and 12,975 of human apo(a) cDNA (McLean et al., Nature, 330:132-137, 1987). The PCR-amplified DNA fragment encoding LK8 was digested with Xho I and BamH I and subsequently cloned into the corresponding sites of the pPIC9 vector (Invitrogen). The plasmid pPIC9 (Invitrogen) was selected for the cloning and expression of the rhLK8 protein because it bears an α-factor secretion sequence that facilitates the secretion of the expressed protein into the medium. The resultant pMBRI-LK8 plasmid was used to express rhLK8 proteins. The cDNA encoding rhLK8 was designed to be located just after the α-factor secretion signal cleavage sites that are cleaved by kex2 protease so that rhLK8 is expressed without any extra amino acid residues that originate from the vector. The cloned rhLK8 DNA sequence was verified by DNA sequencing. Finally, the LK8 gene expression vector 'pMBRI-LK8 (8.25 kb) was constructed (FIG. 1).

Example 1.2

Preparation of a Recombinant Yeast Expressing rhLK8

*Pichia pastoris*, a methylotrophic yeast, was chosen as an expression host, because it can express heterologous protein on a large scale. The *P. pastoris* GS115 strain was used because it secretes very low levels of endogenous host protein, which simplifies the purification of the heterologous protein.

The expression vector for LK8 gene 'pMBRI-LK8' was linearized with a restriction enzyme SacI. The vector was inserted into AOXI gene of the above host strain chromosome by homologous recombination. At that time, electroporation was performed for transformation. A recombinant yeast transformant was selected from histidine-deficient medium by examining colony formation. PCR was performed to confirm if LK8 cDNA was inserted into AOX1 region of chromosome of the selected recombinant transformant. Expression of rhLK8 as a secretory protein was confirmed by Western blotting using culture medium prepared after the induction of gene expression with methanol.

The secreted rhLK8 protein of the present invention was composed of 86 amino acid residues (Glu4225-Ser4310) from apolipoprotein(a) (McLean et al., Nature, 330:132-137, 1987).

Example 1.3

Cultivation of a Recombinant *P. pastoris* Strain

After the selection of the recombinant *Pichia pastoris* strain with the highest LK8 production, the selected strain was seed-cultured in YDP medium (1% yeast extract, 2% peptone, 2% dextrose) for 24 hours with vigorous shaking. Optical density (OD) at 600 nm of the seed culture was 0.8-1.2 when measured after dilution of culture broth by 20 times.

A 75 L fermenter was used for the main culture. The volume of the starting medium was 20 L and the final volume of culture broth was increased to 40 L in the DO-Stat fed-batch fermentation process used for the production of rhLK8. Main culture was performed by inoculating seed culture broth (approximately 10% working volume of the fermenter) into the starting medium. Medium composition for the main culture is indicated in Table 1. When the volume of culture broth was increased to the working volume of the fermenter by the continuous supply of methanol, 10% or more of culture broth was removed, while methanol was being supplied continuously to induce the continuous expression of the protein. This process was repeatedly performed to produce enough LK8 protein to carry out the experiments. Since consumption rate of the carbon source was proportional to increase in the biomass, a DO-Stat fed-batch fermentation process was established to stably maintain the level of dissolved oxygen (DO) in the culture broth to ±20% range of the standard DO by controlling the feeding rate of methanol automatically. After the above high biomass fermentation process over 200 hours, at least 250 mg of LK8 protein per 1 liter of culture broth was produced and secreted into the culture medium.

TABLE 1

Medium composition for main culture

| Type of medium | Component | Concentration |
|---|---|---|
| Medium for main culture | Methanol | 500 g/L |
| | Trace metal solution | 8 ml/L |
| Medium composition of trace metal solution | $CuSO_4 \cdot 5H_2O$ | 4 g/L |
| | KI | 0.3 g/L |
| | $MnSO_4 \cdot H_2O$ | 4 g/L |
| | $NaMo \cdot H_2O$ | 0.1 g/L |
| | $H_3BO_4$ | 0.01 g/L |
| | $CoCl_2$ | 0.1 g/L |
| | $ZnCl_2$ | 3 g/L |
| | $FeSO_4 \cdot H_2O$ | 10 g/L |
| | Biotin | 0.1 g/L |
| | $H_2SO_4$ | 5 ml/L |

Example 2

Purification of rhLK8 Protein Expressed by *P. pastoris*

Because the kringle structure has been reported to be essential for maintaining the anti-angiogenic activity of a kringle-containing protein such as angiostatin (Cao et al., J. Biol. Chem. 271:29461-29467, 1996; Ji et al., FASEB J. 12:1731-1738, 1998), rhLK8 was expressed as a secreted soluble protein and could be easily purified to homogeneity directly from the crude fermentation broth by cation exchange expanded bed adsorption chromatography. Briefly, crude fermentation broth was loaded into Streamline SP (Pharmacia), which was pre-equilibrated with 20 mM sodium phosphate (monobasic) buffer, pH 5.0. The bound proteins were eluted with a linear gradient of NaCl, from 0 to 500 mM, in sodium phosphate buffer, monobasic (pH 7.0). Consecutive SP-Sepharose fast flow chromatography, hydrophobic interaction chromatography (phenyl Sepharose), and reversed phase-high pressure liquid chromatography, in the order stated, were used for further purification.

Figure 2:
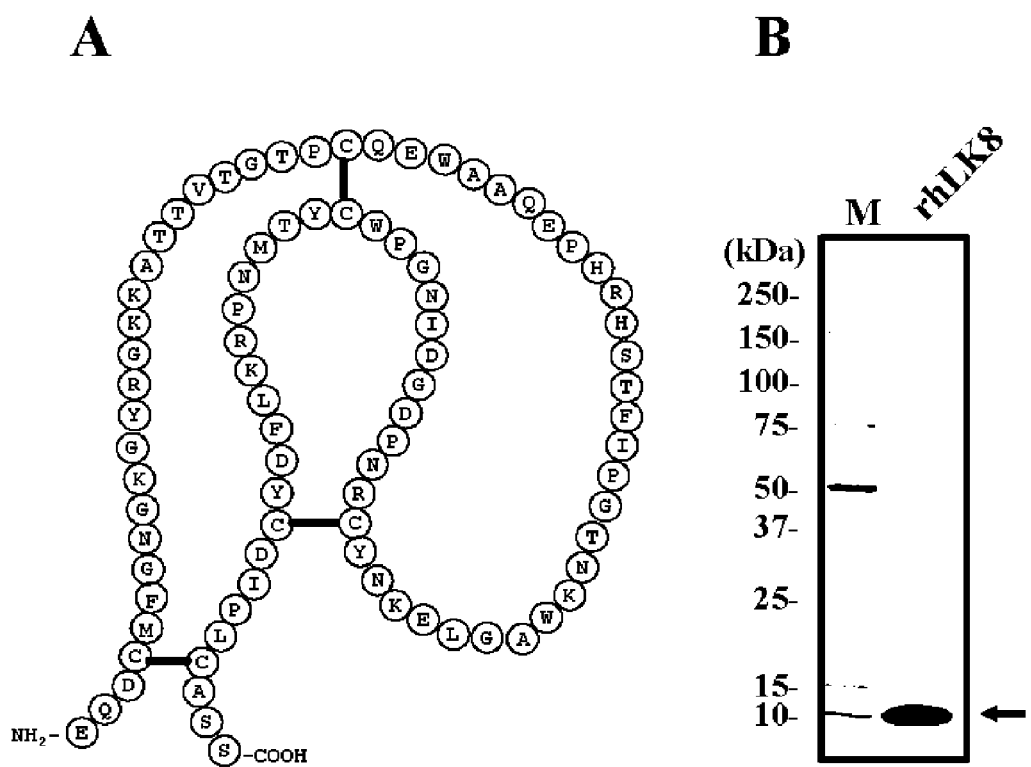

The purified rhLK8 protein migrated on an SDS-PAGE gel as a single band of approximately ~10 kDa under reducing conditions (FIG. 2). The identity of the purified rhLK8 protein was confirmed by protein N-terminal sequencing analysis, since the first six amino acids (EQD-CMF) (SEQ ID NO:7) perfectly matched the expected sequence. Mass spectrometric analysis of the purified protein yielded a molecular weight of 9,664 Da, which is nearly identical to the calculated mass of 9,676 Da.

Example 3 rhLK8 Inhibits Endothelial Cell Migration and Invasion In Vitro

The impact of rhLK8 on endothelial cell migration was determined in a denudation injury model as previously described (Kim et al., J. Biol. Chem. 278:29000-29008, 2003). Briefly, confluent human umbilical vein endothelial cells (HUVECs) were wounded by scraping, then washed and incubated for 8 h in EBM-2 (Clonetics) supplemented with 1% fetal bovine serum (FBS) and 3 ng/ml basic fibroblast growth factor (bFGF), either in the presence or absence of the rhLK8 protein (0.001-1 μM). Control cultures were incubated in EBM-2 plus 1% FBS without bFGF. The cells that migrated into the wounded area were photographed with an Olympus C-3030 digital camera and counted.

The HUVECs migrated into the wounded area in response to bFGF stimulation but this migration was significantly inhibited by rhLK8 in a dose-dependent manner over the range of 0.01-1 μM (FIGS. 3A and 3B). The concentration of rhLK8 required to inhibit the migration of HUVECs by 50% (ED50) was 160 nM as compared with the control cells (FIG. 3B).

To evaluate the effects of rhLK8 on the invasion of endothelial cells, invasion of HUVECs through Matrigel was determined in vitro using Transwell (Costar, Cambridge, Mass., USA) system. Transwell (6.5-mm diameter) polycarbonate membrane inserts with 8.0-μm pores (Costar, Cambridge, Mass., USA) were coated with Matrigel (40 μg/each well; BD Biosciences, Bedford, Mass.) on the top. After adding EBM-2 containing 1% FBS±3 ng/ml bFGF to the bottom chambers, single-cell suspensions of HUVECs in EBM-2 plus 1% FBS were then seeded onto the filters ($5 \times 10^4$ cells per each well) and incubated for 24 h at 37° C., 5% $CO_2$. Filters were then washed and cells on the upper surface were removed with cotton swabs. Cells that had invaded and adhered to the lower surface were fixed with methanol for 15 min and stained with 0.2% (w/v) crystal violet for 15 min. The filters were then extracted with 30% acetic acid. The cells that had invaded were indirectly quantified by determining the absorbance at 595 nm. As shown in FIG. 4, rhLK8 significantly inhibited the bFGF-induced invasion of HUVECS. Invasion of HUVECs through Matrigel was significantly inhibited 39% and 43% after the treatment of 1 μM or 5 μM rhLK8, respectively (p<0.01). Since the migration and invasion of endothelial cells is critical in angiogenesis, the inhibition of endothelial cell motility and invasion could thus be expected to affect the angiogenic process.

Example 4 rhLK8 Affects the Tyrosine Phosphorylation of FAK and Reduces the Formation of Actin Stress Fibers/Focal Adhesions Alteration of the actin-myosin cytoskeleton and the temporal-spatial organization of cell adhesion contacts on the extracellular matrix are crucial events in cell movement. The mitogenic signals generated by growth factor receptors or integrins affect these events. Cell adhesion is controlled by functional complexes called focal adhesions. These complexes consist of integrins, integral membrane proteoglycans, and associated cytoplasmic proteins such as vinculin and paxillin. The proteins in the cell adhesion structures serve as anchors for actin stress fibers, which are responsible for the mechanical forces generated within the cell. The assembly and disassembly of focal adhesions that occurs as the cell converts from an adhesive to a migratory phenotype is a dynamic, complexly regulated process (Parsons et al., Oncogene 19:5606-561 3, 2000; Schlaepfer et al., Prog. Biophys. Mol. Biol. 71:435-478, 1999). Protein tyrosine kinases, and FAK in particular, appear to play a central role in the dynamic regulation of cell adhesion structures.

To investigate the molecular mechanism involved in the rhLK8-mediated inhibition of endothelial cell migration, the effects of rhLK8 on FAK tyrosine phosphorylation was determined as follows. The HUVECs were cultured on glass coverslips and allowed to grow until subconfluency. After serum starvation, the HUVECs were treated with 3 ng/ml bFGF in the presence or absence of 1 µM rhLK8 for 90 min. For immunoblotting, the cells were lysed, quantified for protein concentration and separated on 4-20% pre-cast SDS-PAGE gels. FAK phosphorylation was assessed by immunoblotting with antibodies against phospho-specific FAK (Upstate Biotechnology). The same blot was used to detect the total amounts of FAK by using anti-FAK antibodies (Upstate Biotechnology). For immunostaining, the cells were washed with phosphate-buffered saline (PBS) and fixed with 4% paraformaldehyde on ice for 15 min. For paxillin staining, cells were permeabilized by treatment with 0.4% Triton X-100. The cells were then treated with 1% FBS for 1 h at room temperature and incubated with a mouse monoclonal antibody against paxillin (Signal Transduction Laboratories). Unbound proteins were removed by washing and the cells were subsequently incubated with FITC-labeled secondary antibody for 1 h. TRITC-conjugated phalloidin (Sigma) was used to stain the actin cytoskeleton. The coverslips were then washed three times with Tris-buffered saline containing 0.05% Tween-20 and examined using a fluorescence microscope (Model Axiophot2, Zeiss).

Treatment with bFGF increased the phosphorylated FAK levels (FIG. 5A). However, rhLK8 treatment inhibited bFGF-stimulated FAK tyrosine phosphorylation without affecting the FAK protein levels (FIG. 5A). The possible involvement of FAK in the migration-inhibitory activity of rhLK8 led to examining the cytoskeletal organization of HUVECs treated with bFGF in the presence or absence of rhLK8. Actin stress fibers were visualized by using TRITC-labeled phalloidin. Consistent with the effects of rhLK8 on bFGF-induced FAK phosphorylation, the formation of actin stress fibers was significantly increased by the treatment with bFGF, but this was decreased to background levels when the cells were treated with bFGF and rhLK8 (FIG. 5B). To further characterize the possible mechanism employed, HUVECs were treated with bFGF alone or together with rhLK8 and stained with antibodies specific for paxillin to assess the assembly of focal adhesion complexes. As shown in FIG. 5C, the number of focal adhesion complexes in the bFGF-stimulated HUVECs was significantly inhibited by rhLK8 treatment. Collectively, these results indicate that rhLK8 suppresses endothelial cell migration by inhibiting the bFGF-stimulated phosphorylation of FAK, thus interfering with the formation of focal adhesion complexes and the consequent organization of actin stress fibers.

Example 5 rhLK8 Induces Endothelial Cell Apoptosis

To determine the effects of rhLK8 on endothelial cell apoptosis, HUVEC monolayers were incubated in EBM-2 containing 1% FBS in the presence or absence of 3 ng/ml bFGF and treated with various concentrations of rhLK8 for 12 or 24 h. Endothelial cell apoptosis was assessed by analysis of nuclear morphology after staining with Hoechst 33452 (FIG. 6A). When angiogenic factors were deprived, HUVEC apoptosis was significantly increased by the addition of rhLK8 in a time- and dose-dependent manner (FIG. 6B). The proportion of apoptotic HUVECs decreased by co-treatment with an endothelial cell survival factor, such as bFGF, although rhLK8 still significantly induced apoptosis under these conditions (FIG. 6C).

In order to examine the biochemical characteristics of rhLK8-stimulated HUVEC apoptosis, rhLK8 was tested for its effects on activation of an effector caspase, caspase-3, which is a key step in apoptosis. In HUVECs deprived of angiogenic factors, treatment with rhLK8 reduced expression of the 32-kDa procaspase-3 and produced a corresponding increase in the level of the 20-kDa processed fragment of caspase-3 (FIG. 7A), indicating the activation of caspase-3. The activated caspase-3 appears to play an active role in inducing endothelial cell apoptosis because a cleaved fragment of a caspase-3 substrate, poly ADP-ribose polymerase, was detected at a substantially higher amount in rhLK8-treated HUVECs than in non-treated control HUVECs. Effector caspases are activated downstream of caspase-8 or caspase-9, which are the initiator caspases involved in signaling two distinct apoptotic pathways, namely the death receptor and mitochondrial pathways, respectively (Mow et al., Curr. Opin. Oncol. 13:453-462, 2001). To determine which pathway is responsible for rhLK8-stimulated endothelial cell apoptosis, we tested the effects of rhLK8 on activation of caspase-8 and caspase-9. The level of procaspase-9 was significantly reduced in rhLK8-treated cells when compared with control cells (FIG. 7B), whereas no difference in the level of procaspase-8 was observed between rhLK8-treated and control cells, indicating that the mitochondrial pathway (also termed the intrinsic pathway) was involved. Since the mitochondrial pathway is initiated by the release of cytochrome C and other polypeptides from the mitochondrial intermembrane space to the cytosol, cytochrome C release in rhLK8-treated HUVECs was examined. rhLK8 caused a time-dependent reduction in the level of cytochrome C in the mitochondrial membrane, whereas the level of cytosolic cytochrome C was concomitantly increased (FIG. 7C).

Example 6 rhLK8 Inhibits Angiogenesis In Vivo

It was clearly demonstrated that in vitro rhLK8 blocks endothelial cell migration, which is a fundamental event in angiogenesis. In vivo anti-angiogenic activity of this molecule was also tested.

Example 6.1

Chick Chorioallantoic Membrane (CAM) Assay

To determine whether rhLK8 is an inhibitor of angiogenesis in vivo, the chick CAM assay was used. Fertilized three-day-old eggs were incubated at 37° C., and a window was made after the extraction of ovalbumin. After two days of incubation, a Thermanox coverslip (Nunc) containing rhLK8 or PBS was applied to the CAM of individual embryos. After 48 h, a 20% fat emulsion was injected into the chorioallantois of the embryos and the vessel formation around the Thermanox disk was examined. The presence or absence of an avascular zone larger than 5 mm in diameter in the CAMs tested was scored blindly.

rhLK8 at concentrations of 0.01~10 μg per disk inhibited new embryonic blood vessel growth on the CAM, as measured by the formation of avascular zones (FIG. 8A). The inhibition was dose-dependent (FIG. 8B). At a dose of 10 μg per embryo, rhLK8 inhibited new capillary formation in 79.2% of the eggs tested, whereas inhibition was observed in only 28.4% of the PBS-treated embryos (p<0.00005). No obvious inflammation was detected in any of the embryos tested.

Example 6-2

Matrigel Plug Assay

Figure 9:
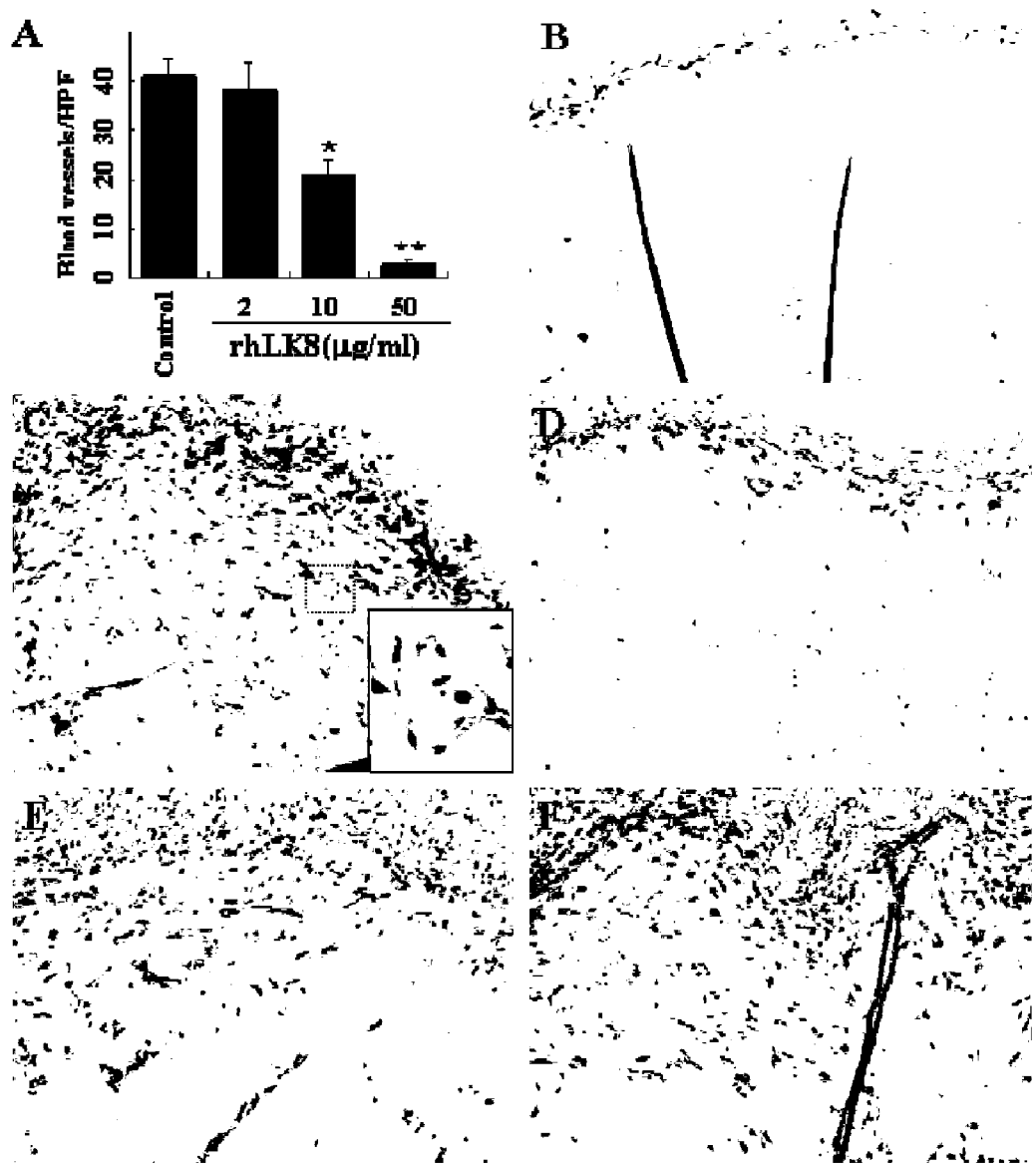

The Matrigel plug assay (Passaniti et al., 67:519-528, 1992) was performed in mice to evaluate the in vivo effect of rhLK8 on the formation of new capillaries. Matrigel was thawed overnight at 4° C. Before injection into C57BL/6 mice, it was mixed with 60 units/ml heparin (Sigma), 10 ng/ml bFGF, and either 0, 2, 10, or 50 μg/ml rhLK8. Control groups received heparin only. The Matrigel mixture (500 μl) was injected subcutaneously by using a 21-gauge needle. After 7 days, the mice were sacrificed and the Matrigel plugs were removed and fixed in 4% paraformaldehyde in PBS. The plugs were embedded in paraffin, sectioned, and stained with hematoxylin and eosin (H&E). The sections were examined by light microscopy and the blood vessels infiltrating into the Matrigel plugs were counted. Matrigel plugs without bFGF showed no capillary infiltration (FIG. 9B) but significant infiltration of blood vessels was observed in Matrigel plugs containing 100 ng/ml bFGF (FIG. 9C). The bFGF-induced formation of capillaries in the Matrigel plugs was inhibited by rhLK8 in a dose-dependent manner (FIG. 9A). rhLK8 at 10 or 50 μg/ml reduced the number of blood vessels by 49 or 93%, respectively, as compared to the untreated controls (FIGS. 9D and 9E), thus indicating that rhLK8 is a potent inhibitor of neovascularization in vivo.

Example 7

Effects of rhLK8 on the Growth of Tumor Cells In Vivo

Example 7.1 rhLK8 Suppresses the Growth of A549 Human Lung Carcinoma and PC-3 Human Prostate Carcinoma Xenografts The potential anti-angiogenic activities of rhLK8 are expected to be useful in the treatment of angiogenesis-dependent malignancies such as cancer. To assess the anti-angiogenic and anti-tumor activities of rhLK8, A549 human lung cancer cells or PC-3 human prostate carcinoma cells were subcutaneously implanted into mice and the effects of rhLK8 on the tumor growth was determined. Female 6-week-old athymic Balb/c nu/nu nude mice (Charles River Japan, Yokohama, Japan) were used for tumor studies. Approximately $1 \times 10^7$ human lung carcinoma cells (A549) or $5 \times 10^6$ human prostate carcinoma cells (PC-3) in the logarithmic growth phase were harvested and resuspended in phosphate-buffered saline (PBS). A single cell suspension in a volume of 100 μl was implanted subcutaneously in the flank of each animal. When the implanted tumors were palpable, mice in the treatment group (n=5) were first treated by intraperitoneal injections with rhLK8 (either 100 or 50 mg/kg/day), rhLK68 (50 mg/kg/day), or angiostatin (recombinant human plasminogen kringle 1-3; 50 mg/kg/day). Control mice (n=5) received daily injections of PBS. Primary tumors were measured with calipers on the days indicated. Tumor volumes were calculated according to the formula width$^2 \times$length$\times 0.52$. Significant inhibition of A549 human lung carcinoma growth, 70% and 58% versus controls, was observed in animals treated with 100 (FIG. 10A; p<0.001) or 50 mg/kg/day rhLK8 (FIG. 10B; p<0.05), respectively. When compared with the anti-tumor activities of rhLK8 with those of angiostatin or rhLK68, tumor growth suppression induced by rhLK8 was comparable to that induced by either angiostatin or rhLK68. In addition, tumor growth suppression by systemic treatment with rhLK8 (50 mg/kg/day) was also observed in tumor xenografts formed by PC-3 human prostate carcinoma cells (FIG. 10C).

In order to examine the basis of tumor growth suppression by rhLK8, tumor tissues from control and rhLK8-treated animals bearing A549 human lung carcinoma xenografts were analyzed for neovascularization, proliferation, apoptosis, and the expression of angiogenic factors. The overall histological appearance of control and rhLK8-treated tumor tissues was similar. In general, the tumors had several coagulative necrotic areas in their center and active cellular proliferation in their periphery. However, the necrotic areas were more extensive in the rhLK8-treated tumor tissues. We next performed vWF immunostaining of tumor sections to analyze the effects of rhLK8 on tumor angiogenesis. Tumors of rhLK8-treated animals showed a significant reduction in blood vessels compared to the numbers observed in the control group (p<0.05) (FIGS. 11a1 and 11a2; and FIG. 12A). Thus, the suppression of tumor growth by rhLK8 appears to be mediated by inhibiting angiogenesis in tumor tissues. Tumor sections were stained with anti-PCNA (FIGS. 11b1 and 11b2) and subjected to the in situ labeling of fragmented DNA using the TUNEL method (FIGS. 11c1 and 11c2) to determine proliferation and apoptosis, respectively. The proliferative and apoptotic indices of cells within areas of viable tumor were estimated by scoring the tissues under a light microscope. The proliferative index was similar for the control and rhLK8-treated tumors (FIG. 12B). However, the apoptotic index was significantly increased in the rhLK8-treated tumors (FIG. 12C). Since angiogenic factors, such as VEGF, play a critical role in tumor angiogenesis, sections were immunostained to determine the effects of rhLK8 treatment on tumor VEGF expression. Tumor tissues from the rhLK8-treated animals had a significantly reduced expression of VEGF protein compared to control tissues (FIGS. 11d1 and 11d2; and FIG. 12D).

Example 7.2 rhLK8 Inhibits the Growth of LS174T Human Colon Carcinoma Xenograft in Nude Mice Female 5-week-old athymic BALB/c nu/nu nude mice (Charles River Japan, Yokohama, Japan) were used for tumor studies. Approximately $5\times10^6$ human colorectal carcinoma cells (LS174T) in the logarithmic growth phase were harvested and resuspended in phosphate-buffered saline (PBS). A single cell suspension in a volume of 100 µl was implanted subcutaneously in the flank of each animal. In the treatment group (n=6), mice were first treated by intraperitoneal injections with rhLK8 (50, 10, 2 mg/kg/day) four days after the implantation. These injections were continued for 28 days. Control mice (n=6) received injections of PBS daily. Primary tumors were measured with calipers on the days indicated. Tumor volumes were calculated according to the formula width$^2\times$length$\times 0.52$. A dose-dependent delay in tumor growth was observed in rhLK8-treated animals. Tumor volumes were significantly decreased by 66% (FIGS. 13A and 13B, $p<0.01$) versus controls in animals treated with 50 mg/kg rhLK8, while the decrease in tumor volume in animals treated with 10 or 2 mg/kg/day rhLK8 did not reach statistical significance. A significant decrease (~50%) in tumor weight was additionally observed in mice treated with 50 mg/kg rhLK8 ($p<0.05$) (FIG. 13C).

Example 7.3 rhLK8 Prolongs the Overall Survival of Hosts that have been Implanted Intracecally with KM12SM Human Colon Carcinoma Cells Mice 5-week-old athymic BALB/c nu/nu nude mice (Charles River Japan, Yokohama, Japan) were anesthetized with ketamine/xylazine, and the abdomen was prepared for sterile surgery. A small abdominal incision was made, and the cecum was exteriorized and isolated on sterile gauze. Viable KM12SM human colon carcinoma cells ($1\times10^6$ cells in 30 µl PBS) were injected into the cecal wall from the serosal side with a 30-gauge needle. The formation of a visible bulla between the submucosal and subserosal tissues and the lack of extracecal leakage of fluid were the criteria for a successful injection. The cecum was returned to the abdominal cavity and the wound was closed in one line with metal wound clips. Mice were randomly divided into two groups and were used in survival experiments. In the treatment group (n=4), rhLK8 (50 mg/kg body weight, daily) was administered intraperitoneally. The control group of mice (n=5) was given equal volume of saline. The fraction of surviving animals was monitored for 78 days. As shown in FIG. 14, systemic treatment with rhLK8 significantly improved host survival in rhLK8-treated animals, compared with control animals (log-rank test; $p<0.05$).

Example 8

Effects of rhLK8 on the Metastasis of Tumor Cells

Example 8.1

Suppression of Colorectal Cancer Liver Metastasis and Extension of Survival by rhLK8

Given that angiogenesis is critical for tumor cell metastasis as well as solid tumor growth, the effects of rhLK8 on the liver metastasis of colorectal cancer cells were examined using an animal model for experimental liver metastasis. Athymic BALB/c nude mice were anaesthetized intraperitoneally with ketamine/xylazine (Sigma). The spleen was then exteriolized through a left lateral flank incision. $3\times10^5$ cells of LS174T human colorectal carcinoma in 100 µl of PBS were injected into the spleen parenchyma using a 27-gauge needle. The peritoneum and skin were closed in two layers with metal clip. From the day of tumor inoculation, mice were administered intraperitoneally 50, 10, 2, or 0.4 mg/kg rhLK8 per day. Mice were sacrificed fourteen days after tumor cell implantation, and livers were collected for the analysis of the surface nodule number of liver metastases or subjected to histologic and immunohistochemical examination. In addition, control and rhLK8 (50 or 10 mg/kg)-treated mice were employed in survival experiments (n=10/each group).

Mice in the rhLK8 treatment group that have received daily intraperitoneal injections of 50, 10, 2 mg/kg rhLK8 developed significantly fewer liver metastases in a dose-dependent manner ($p<0.05$ and $p<0.01$ for groups of mice given 50 or 10 mg/kg rhLK8, respectively, FIGS. 15A and 15B). Suppression of liver metastasis by rhLK8 was further analyzed with liver tissues stained by hematoxylin and eosin (H&E). Significantly higher hepatic areas were replaced by metastasized tumors in the livers of control mice than rhLK8-treated mice (FIG. 15C). Numbers of liver metastases in the livers of rhLK8-treated mice were significantly decreased in a dose-dependent manner when compared to those of control mice ($p<0.01$ and $p<0.05$ for experimental groups treated with 50 or 10 mg/kg/day rhLK8, respectively).

In agreement of Paku and Lapis, two distinct subgroups of metastasis were recognized according to their microvascular connection and angiogenic pattern: (1) sinusoidal-type metastases with convoluted vessels lacking immunohistochemically detectable basement membrane, in which metastatic cells are located between the hepatocytes and sinusoidal endothelial cells and (2) portal-type, located in the vicinity of portal tracts, characterized by a high microvessel density and positive staining for a basement membrane (Paku et al., Am. J. Pathol. 143:926-936, 1993) (FIG. 15D). As shown in FIG. 17B, sinusoidal-type metastasis density significantly decreased in rhLK8-treated mice compared with saline-treated mice, whereas portal type metastasis density did not significantly vary in the LK8 treated mice compared with saline-treated mice. The ratio of sinusoidal-type versus portal type metastasis was 1.6 in saline-treated mice and 0.9 in rhLK8 (50 mg/kg)-treated mice (FIG. 15E), suggesting the preferential action of rhLK8 on the sinusoidal type-metastases.

To assess whether the suppression of metastasis by rhLK8 translates into a survival benefit, a survival experiment was conducted as follows. Mice were injected intrasplenically with LS174T human colon carcinoma cells and were then treated intraperitoneally with 2, 10, or 50 mg/kg rhLK8. The fraction of surviving animals was monitored for ~70 days. As depicted in FIG. 16, systemic treatment with rhLK8 significantly improved host survival in rhLK8-treated animals, compared with control animals (log-rank test; $p<0.005$ and $p<0.0001$ for animals treated with 10 or 50 mg/kg rhLK8 versus control, respectively). The median survival was 29, 41 and 46 days in groups of animals treated with saline, 10 mg/kg rhLK8 and 50 mg/kg rhLK8, respectively.

Example 8.2

Suppression of Experimental Pulmonary Metastasis of B16F10 Melanoma Cells by rhLK8

Figure 17:
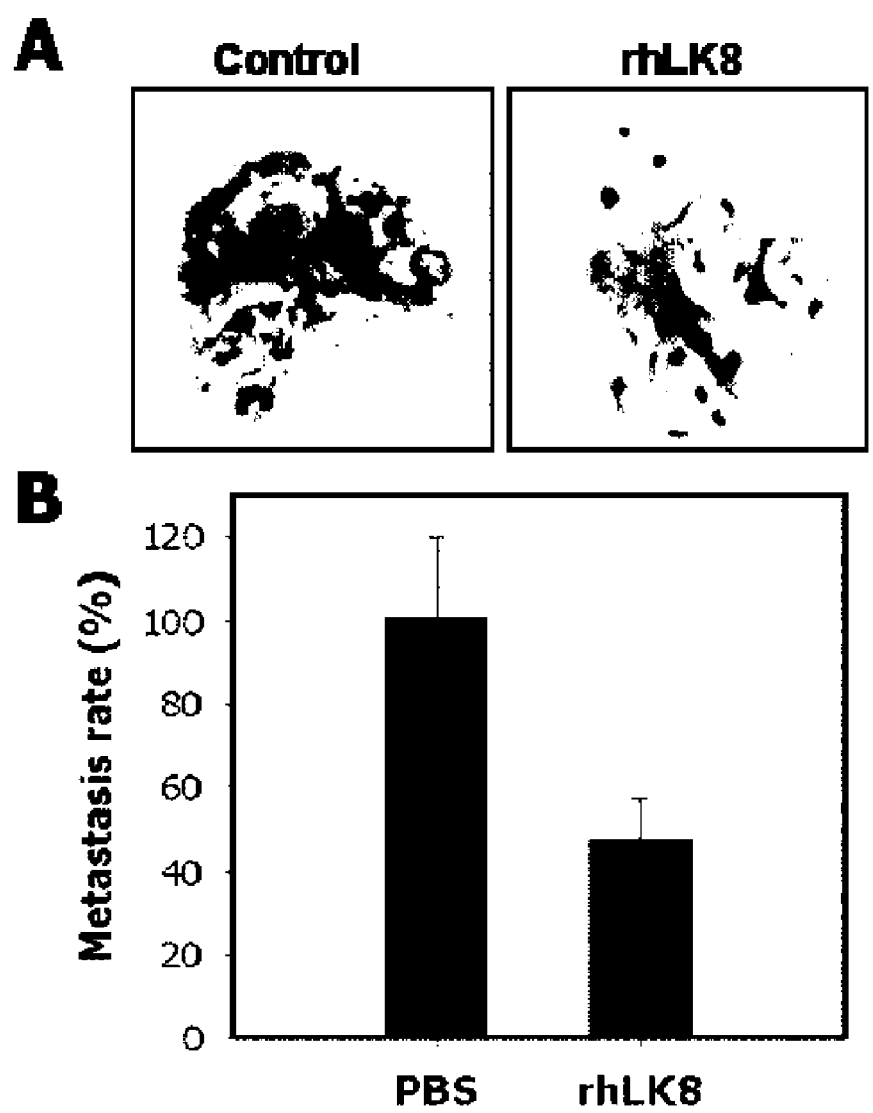

Six-week-old specific-pathogen-free C57BL/6 mice (Charles River Japan, Yokohama, Japan) were injected via the tail vein with $2 \times 10^5$ B16F10 murine melanoma cells in 100 µl PBS. Groups of 5 mice were treated with 1 mg/kg/day of LK8 protein from the day of injection of the B16F10 cells. Doses were administered twice daily for 14 days intraperitoneally, after which all mice were sacrificed, the lungs were removed and fixed in Bouin's solution (Sigma). The number of surface metastases in each animal was counted under a stereo-microscope. As shown in FIG. 17, the number of colonies on the surface of the lungs from the experimental group of mice treated with 1 mg/kg/day rhLK8 was significantly lower than the number of surface colonies on the lungs from control group of mice and showed 53% metastasis inhibition, compared to the control group.

Example 9 rhLK8 Protein Acute Toxicity Test 5-week-old, specific-pathogen-free SD (Sprague Dawley) line rats were used in the test for acute toxicity. Rats were divided into 5 groups, and 5 rats per each group were administered once with rhLK8 protein by a dosage of 260 mg/kg, 364 mg/kg, 510 mg/kg, 714 mg/kg and 1,000 mg/kg, respectively, by intravenous injection (Table 2). For 14 days after injecting rhLK8 protein, parameters such as death, clinical symptoms and weight change in the rats were observed. Hematological tests and biochemical tests of blood were performed, and any abnormal signs in the gastrointestinal organs of chest and abdomen were checked by eye during autopsy. The observations showed that weak toxicity was detected in the group administered with 1000 mg/kg of rhLK8 protein, but no toxicity or death was found in other dosage groups as measured by weight change, blood test, hematological tests, autopsy, and so on. Therefore, the rhLK8 protein used in this experiment appears to be a safe substance for administration since it did not cause any toxic change in rats up to the level of 1,000 mg/kg, whereas its estimated LD50 values are much greater than 1,000 mg/kg in rats (Table 2).

were injected intrasplenically with LS174T human colon carcinoma cells ($3 \times 10^5$ cells), randomized into four groups, and treated with saline rhLK8 (10 mg/kg, daily), 5-FU (8 mg/kg in a day; over days 0-4), or the combination of rhLK8 and 5-FU. On day 17 after tumor cell injection, livers were removed and the surface tumor nodules were counted. Treatment with rhLK8 alone, 5-FU alone, and their combination significantly inhibited hepatic metastasis by 61% ($p<0.02$; n=5), 53% ($p<0.02$; n=4), 86% ($p<0.005$; n=4), respectively, as compared with the saline control (n=5) (FIG. 18A). Moreover, the combined treatment of rhLK8 and 5-FU significantly improved host over that observed by either treatment alone (FIG. 18B).

Example 11

Expression and Purification of Recombinant Human LK68 Protein cDNA encoding LK68, which consists of human apo(a) kringle domains KIV36, KIV37 and KV38, was amplified by PCR using a human liver cDNA library as the template with the oligonucleotide primers 5'-TCCATATGAAAAGC-CCTGTGGTCCAGGAT-3' (SEQ ID NO:8) and 5'-CGG-GATCCTTAAGAGGATGCACA-3' (SEQ ID NO:9), which contains linkers with Nde I and BamH I restriction sites, respectively. The sequence of the cDNA is as follows: 5'-aaaagccctg tggtccagga ttgctaccat ggtgatggac ggagttatcg aggcatatcc tccaccactg tcacaggaag gacctgtcaa tcttggtcat ctatgatacc acactggcat cagaggaccc cagaaaacta cccaaatgct ggcctgaccg agaactactg caggaatcca gattctggga aacaaccctg gtgttacaca accgatccgt gtgtgaggtg ggagtactgc aatctgacac aatgctcaga aacagaatca ggtgtcctag agactcccac tgttgttcca gttccaagca tggaggctca ttctgaagca gcaccaactg agcaaacccc tgtggtccgg cagtgctacc atggtaatgg ccagagttat cgaggcacat tctccaccac tgtcacagga aggacatgtc aatcttggtc atccatgaca ccacaccggc atcagaggac cccagaaaac taccaaatg atggcctgac aatgaactac tgcaggaatc cagatgccga tacaggcct tggtgtttta ccacggaccc cagcatcagg tgggagtact gcaacctgac gcgatgctca gacacagaag ggactgtggt cgctcctccg actgtcatcc aggttccaag cctagggcct cct-tctgaac aagactgtat gtttgggaat gggaaaggat accggggcaa gaag-gcaacc actgttactg ggacgccatg ccaggaatgg gctgcccagg agc-cccatag acacagcacg ttcattccag ggacaaataa atgggcaggt ctggaaaaaa attactgccg taaccctgat ggtgacatca atggtccctg gtgc-tacaca atgaatccaa gaaaactttt tgactactgt gatatccctc tctgtgcatc

TABLE 2

The number of deaths according to days after LK8 protein administration

| Amount of administration (mg/kg) | Number of deaths/Total test rats | Days after LK 8 protein administration |||||||||||||||
|---|---|---|---|---|---|---|---|---|---|---|---|---|---|---|---|
| | | 0 | 1 | 2 | 3 | 4 | 5 | 6 | 7 | 8 | 9 | 10 | 11 | 12 | 13 | 14 |
| 260 | 0/5 | 0 | 0 | 0 | 0 | 0 | 0 | 0 | 0 | 0 | 0 | 0 | 0 | 0 | 0 | 0 |
| 364 | 0/5 | 0 | 0 | 0 | 0 | 0 | 0 | 0 | 0 | 0 | 0 | 0 | 0 | 0 | 0 | 0 |
| 510 | 0/5 | 0 | 0 | 0 | 0 | 0 | 0 | 0 | 0 | 0 | 0 | 0 | 0 | 0 | 0 | 0 |
| 714 | 0/5 | 0 | 0 | 0 | 0 | 0 | 0 | 0 | 0 | 0 | 0 | 0 | 0 | 0 | 0 | 0 |
| 100 | 3/5 | 0 | 0 | 3 | 0 | 0 | 0 | 0 | 0 | 0 | 0 | 0 | 0 | 0 | 0 | 0 |

Example 10

Effect of rhLK8 and/or Chemotherapy on Liver Metastasis of Colon Carcinoma Cells To investigate the activity of rhLK8, chemotherapy with 5-FU, and the combination against hepatic metastasis, mice ctct-3' (SEQ ID NO:10) corresponding to the amino acid sequence: Lys Ser Pro Val Val Gln Asp Cys Tyr His Gly Asp Gly Arg Ser Tyr Arg Gly Ile Ser Ser Thr Thr Val Thr Gly Arg Thr Cys Gln Ser Trp Ser Ser Met Ile Pro His Trp His Gln Arg Thr Pro Glu Asn Tyr Pro Asn Ala Gly Leu Thr Glu Asn Tyr Cys Arg Asn Pro Asp Ser Gly Lys Gln Pro Trp Cys Tyr Thr Thr Asp Pro Cys Val Arg Trp Glu Tyr Cys Asn Leu Thr Gln Cys Ser Glu Thr Glu Ser Gly Val Leu Glu Thr Pro Thr Val Val Pro Val Pro Ser Met Glu Ala His Ser Glu Ala Ala Pro Thr Glu Gln Thr Pro Val Val Arg Gln Cys Tyr His Gly Asn Gly Gln Ser Tyr Arg Gly Thr Phe Ser Thr Thr Val Thr Gly Arg Thr Cys Gln Ser Trp Ser Ser Met Thr Pro His Arg His Gln Arg Thr Pro Glu Asn Tyr Pro Asn Asp Gly Leu Thr Met Asn Tyr Cys Arg Asn Pro Asp Ala Asp Thr Gly Pro Trp Cys Phe Thr Thr Asp Pro Ser Ile Arg Trp Glu Tyr Cys Asn Leu Thr Arg Cys Ser Asp Thr Glu Gly Thr Val Val Ala Pro Pro Thr Val Ile Gln Val Pro Ser Leu Gly Pro Pro Ser Glu Gln Asp Cys Met Phe Gly Asn Gly Lys Gly Tyr Arg Gly Lys Lys Ala Thr Thr Val Thr Gly Thr Pro Cys Gln Glu Trp Ala Ala Gln Glu Pro His Arg His Ser Thr Phe Ile Pro Gly Thr Asn Lys Trp Ala Gly Leu Glu Lys Asn Tyr Cys Arg Asn Pro Asp Gly Asp Ile Asn Gly Pro Trp Cys Tyr Thr Met Asn Pro Arg Lys Leu Phe Asp Tyr Cys Asp Ile Pro Leu Cys Ala Ser Ser (SEQ ID NO:11). The amplified 924-bp fragment, which spans nucleotides 12,052 to 12,975 (McLean et al., Nature, 330:132-137, 1987), was digested with Nde I and BamH I and cloned into pre-digested *E. coli* expression vector pET-11a (Novagen) to make pET-11a/LK68.

*E. coli* BL21 (DE3) cells containing pET-11a/LK68 were grown in LB broth containing ampicillin (50 µg/ml) at 37° C. with shaking. When the $OD_{600}$ of the culture reached 0.5, isopropyl β-D-thiogalactopyranoside (IPTG) was added to a final concentration of 1 mM. Cells were incubated for an additional 3 h and then harvested by centrifuging at 8,000×g for 20 min at 4° C. The cells were disrupted by incubating with lysozyme (0.2 mg/ml) and DNase (2 µg/ml) in 20 mM Tris-HCl (pH 7.5) containing 0.2% Triton X-100 at room temperature for 30 min, and the cell lysate was centrifuged at 10,000×g for 20 min. The isolated inclusion bodies were washed several times with 2% (w/v) sodium deoxycholate in Tris-HCl (pH 8.0) and solubilized in 7 M urea containing 100 mM β-mercaptoethanol. Refolding was accomplished in 20 mM Tris-HCl (pH 8.0) buffer in the presence of reduced and oxidized glutathione and L-lysine, and the solution was dialyzed against 20 mM sodium phosphate (pH 7.5). The refolded proteins were applied to a lysine-Sepharose 4B column, and the bound proteins were eluted with 0.2 M ε-aminocaproic acid (ε-ACA) in 20 mM sodium phosphate buffer (pH 7.5). Fractions containing LK68 were pooled, concentrated, and loaded onto a Sephadex G-25 column (2.5×20 cm) to remove ε-ACA. Chromatography with polymyxin-B beads (Sigma) was performed to eliminate any endotoxins. Recombinant LK68 protein was highly expressed in *E. coli* BL21 (DE3) as an inclusion body and accumulated to comprise about 20-30% of the total cellular protein (FIG. 19A). rhLK68 proteins were solubilized from inclusion bodies, refolded, and purified to homogeneity using lysine-Sepharose 4B affinity chromatography. The presence of a functional lysine-binding site in the purified rhLK68 indicates that rhLK68 was folded in the same way as the native apo(a) kringle domains. Purified rhLK68 migrated as a single ~37-kDa band on SDS-PAGE under reducing conditions (FIG. 19B). The identity of purified rhLK68 was confirmed by N-terminal amino acid sequence analysis.

Example 11

Figure 20:
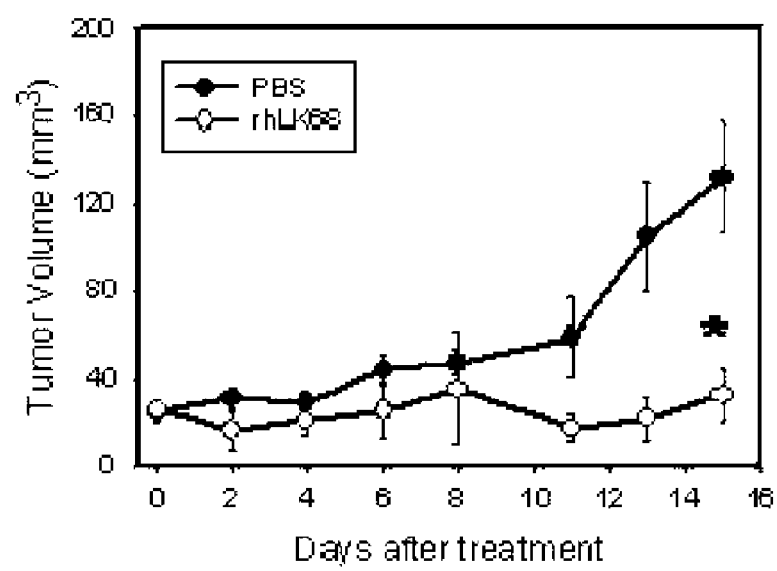
Figure 20:
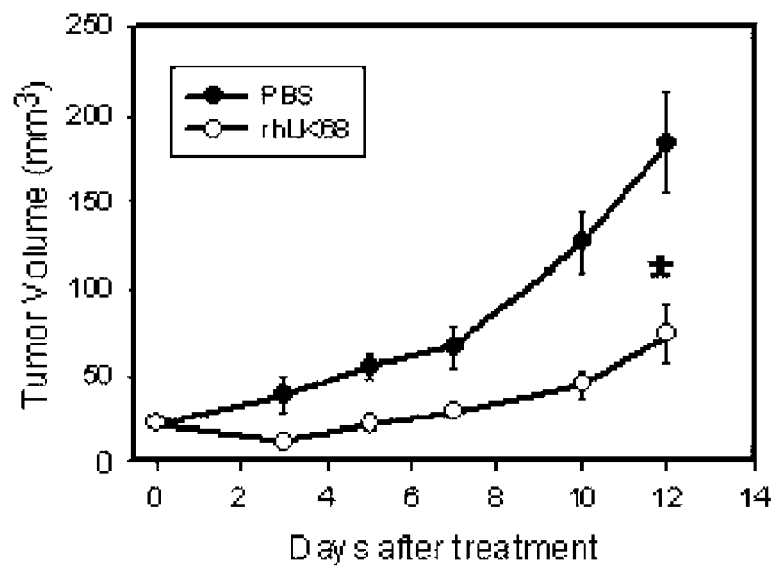

Suppression of Primary Tumor Growth by Systemic Administration of rhLK68 rhLK68 exhibited a dose-dependent inhibition of bFGF-stimulated human umbilical vein endothelial cell proliferation and migration in vitro, and inhibited the neovascularization in chick chorioallantoic membranes in vivo. The ability of rhLK68 to abrogate the activation of extracellular signal-regulated kinases through a protein tyrosine phosphatase-dependent pathway appears to be responsible for rhLK68-mediated anti-angiogenesis. To evaluate whether rhLK68 can suppress tumor growth prior to expansion of tumor, the following animal experiments were carried out. Four-week-old female BALB/c nu/nu nude mice (Charles River, Japan) were housed in a sterile environment. Cages, bedding, food, and water were all autoclaved. The mice were maintained on a 12-h light/12-h dark cycle. Human lung cancer cells (cell line A549) or human colon cancer cells (cell line HCT-15) were purchased from the Korean Cell Line Bank (Seoul, Korea) and were maintained in RPMI 1640 medium supplemented with 10% heat-inactivated FBS and antibiotics. Either $2 \times 10^7$ A549 or HCT-15 cells were subcutaneously injected into the nude mice in the proximal midline of the dorsa. When tumors were palpable at day 7 after tumor implantation, mice were randomly divided into two groups. In the treatment group, rhLK68 (100 mg/kg body weight, daily) was administered subcutaneously. The control group was treated with PBS only. Treatment was continued for 12 (HCT-15) or 15 (A549) days, at which point all mice were sacrificed and the tumors were removed. The tumor size was measured every 2-3 days and the tumor volume was determined using the formula: width$^2$×length× 0.52. Treatment with rhLK68 resulted in a significant suppression of primary tumor growth as shown in FIG. 20. The ratio of mean tumor volume of treated mice over control mice (T/C) was 0.247 ($p<0.02$) in A549 (FIG. 20A) and 0.403 ($p<0.02$) in HCT-15 primary tumors (FIG. 20B), respectively.

Example 12

Decreased Expression of Angiogenic Factors in rhLK68-treated Tumor Tissues

Figure 21:
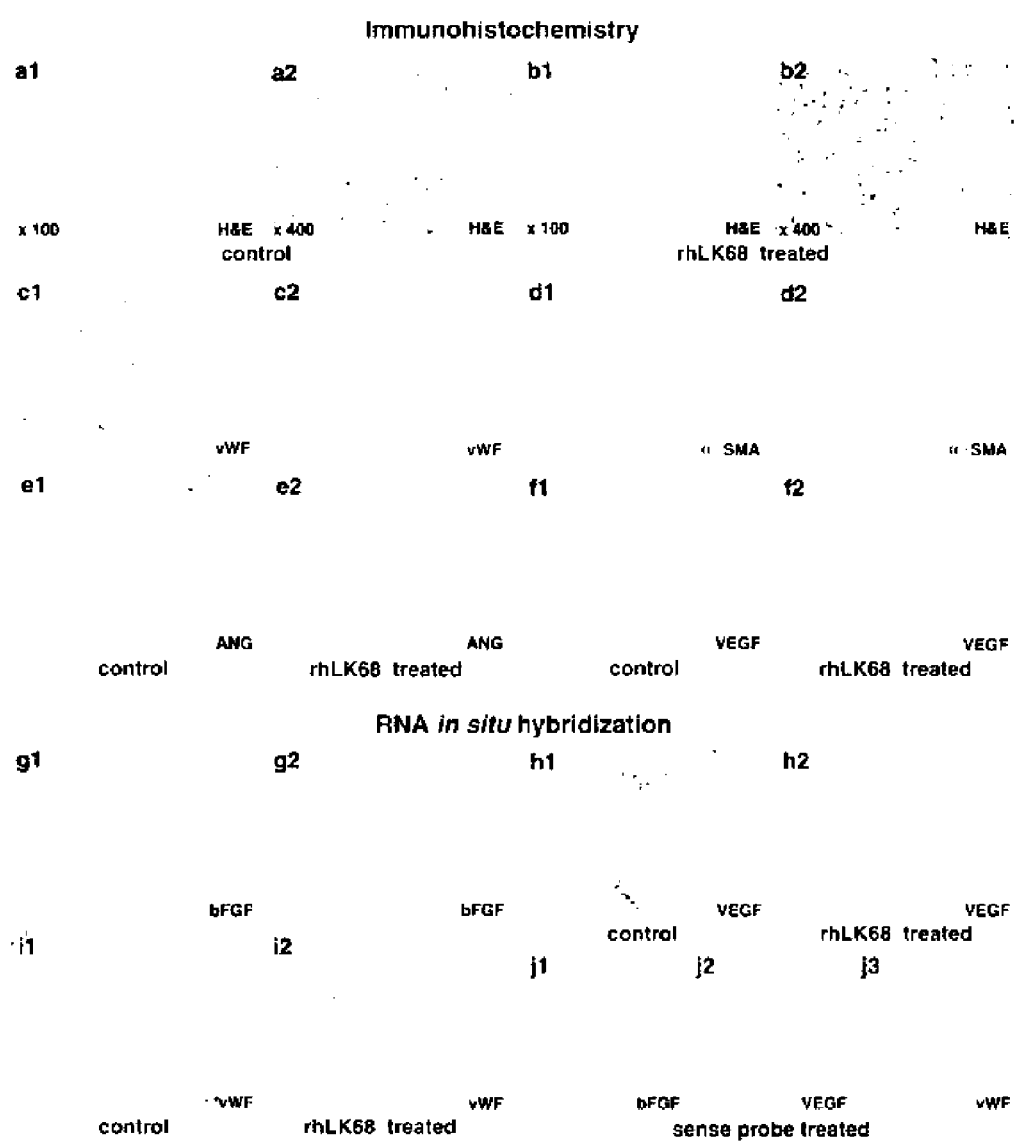

To evaluate the consequences of rhLK68 treatment, implanted tumor tissues were examined by immunostaining and RNA in situ hybridization. Hematoxylin and eosin staining showed that HCT-15 cells from control mice were highly proliferative especially around the peripheral region of tumor and the cells were distributed in a fairly compact and dense fashion and became somewhat less dense in the tumor center (FIGS. 21*a*1 and 21*a*2). In contrast, tumor cells from rhLK68-treated mice were loosely arranged even near the periphery of the tumor and were frequently separated by collagenous fibrous tissues, with multiple necrotic spots in the tumor parenchyma (FIGS. 21*b*1 and 21*b*2). To examine the effect of rhLK68 on tumor neovascularization, an established endothelial cell marker vWF was immunostained (FIGS. 21*c*1 and 21*c*2). Close examination of the entire region of tumor tissues (HCT-15) showed uneven distribution of vessels in both tumors from the control and the rhLK68-treated mice. In tumors from the control mice, vWF-positive cells were usually found in the actively proliferating peripheral region of tumor, whereas the middle of tumor parenchyma, where tumor cells are enlarged and less dense, showed scant distribution of vessels. In contrast, tumor from the rhLK68-treated mice showed only a few vWF-positive cells even in the periphery of tumor tissues where cells are almost a half dense as the control tumor and appear to be in necrotic state as well. The vWF-positive cells are almost undetectable in the core region of tumor from the treated mice. Estimation of vWF-positive cells in the 100 randomly selected fields in the peripheral region of tumors from the control and the rhLK68-treated mice provided some measure of vascularity affected by rhLK68 treatment. Only a small fraction (15~20%) of vWF-positive cells remained in tumors from the treated mice in comparison with the control. The decreased expression of vWF was also confirmed at the transcriptional level by RNA in situ hybridization (FIGS. 21i1 and 21i2), which indicated that microvessel infiltration was significantly reduced by rhLK68 treatment. Similarly, the results from immunostaining of α-SMA showed well-developed vascular structure in tumor tissues from control mice but sparse distribution of blood vessels in tumor tissues from rhLK68-treated mice (FIGS. 21d1 and 21d2). Since the implanted tumor cells are able to produce high levels of angiogenic factors such as angiogenin, bFGF, and VEGF, which switch on the angiogenic phenotype in the tumor implant, the effect of rhLK68 on the expression of these factors was determined. Interestingly, the expression of angiogenin (FIG. 21, e1 and e2), VEGF (FIG. 21, f1 and f2 for protein, and h1 and h2 for mRNA), and bFGF (FIG. 21, g1 and g2) was dramatically decreased in rhLK68-treated tumor tissues compared to control mice as assessed by immunohistochemical and RNA in situ hybridization analyses. Consistent results were observed in implanted tumor tissues of A549 human lung cancer cells.

Example 13

Systemic Treatment of rhLK68 Inhibits the Pulmonary Metastasis of B16F10 Melanoma Cell Lines To test whether rhLK68 treatment can suppress the metastasis of tumor cells as well as solid tumor growth, six-week-old specific-pathogen-free C57BL/6 mice were injected via the tail vein with $2 \times 10^5$ B16F10 cells in 100 μl PBS. Groups of 5 mice were treated with 10 mg/kg/day of LK68 protein from the day of injection of the B16F10 cells. Doses were administered daily for 14 days intraperitoneally, after which all mice were sacrificed, the lungs removed and fixed in Bouin's solution (Sigma). The number of surface metastases in each animal was counted under a stereomicroscope. Systemic treatment of rhLK68 significantly inhibits the pulmonary metastasis of B16F10 cells, as the number of metastases on the lungs from rhLK68-treated mice is significantly lower than that observed in the lungs from control mice (FIGS. 22A and 22B, $p<0.05$). Histologic examination of the tumor-bearing lungs showed that lung metastases in the rhLK68-treated lung tissues were relatively small and mainly observed in the area near the large blood vessels, while metastases in the lung from control mice were large and evenly distributed in the entire lung tissues (FIG. 22C). Moreover, destruction of lung parenchymal tissue was more obvious in the lung tissues from control mice than that observed in the LK68-treated lung tissues.

INDUSTRIAL APPLICABILITY

As explained hereinbefore, LK8 and LK68 proteins have an inhibitory effect on metastasis, in particular, on the growth of human prostate cancer, lung cancer, colon cancer and rectal cancer as being systemically administered. Thus, an anticancer agent containing LK8 or LK68 protein of the present invention can be effectively used as a treatment agent for a primary tumor or a metastasis inhibitor.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims.

What is claimed is:

1. A method of reducing tumor growth comprising contacting the tumor with a tumor growth reducing effective amount of a composition comprising LK8 protein consisting of the amino acid sequence of SEQ ID NO:2 or LK68 protein consisting of the amino acid sequence of SEQ ID NO:11 and a pharmaceutically acceptable carrier thereof to a subject having tumor.

2. The method according to claim 1, wherein the tumor is carcinoma.

3. The method according to claim 2, wherein the tumor is prostate cancer, melanoma, colon cancer, rectal cancer, liver cancer or lung cancer.

4. The method according to claim 1, wherein the tumor is primary tumor.

5. The method according to claim 1, wherein the effective amount of LK8 or LK68 protein is a dose of 0.1 to 100 mg/kg.

6. The method according to claim 5, wherein the effective amount of LK8 or LK68 protein is a dose of 1 to 50 mg/kg.

7. A method for inhibiting metastasis of cancer comprising administering a metastasis inhibition effective amount of a composition comprising LK8 protein consisting of the amino acid sequence of SEQ ID NO:2 or LK68 protein consisting of the amino acid sequence of SEQ ID NO:11 and a pharmaceutically acceptable carrier thereof to a subject in need thereof.

8. The method according to claim 7, wherein the cancer is carcinoma.

9. The method according to claim 8, wherein the carcinoma is liver cancer, lung cancer, melanoma, prostate cancer, colon cancer or rectal cancer.

10. The method according to claim 7, wherein the effective amount of LK8 or LK68 protein is a dose of 0.1 to 100 mg/kg.

11. The method according to claim 10, wherein the effective amount of LK8 or LK68 protein is a dose of 1 to 50 mg/kg.

12. A method for inhibiting metastasis of cancer comprising administering a combination of component (i) a composition comprising LK8 protein consisting of the amino acid sequence of SEQ ID NO:2 or LK68 protein consisting of the amino acid sequence of SEQ ID NO:11 and a pharmaceutically acceptable carrier thereof; and component (ii) radiation therapy, immunotherapy or chemotherapy to a subject in need thereof, with sufficient dosage or amount of the combination of component (i) and component (ii) to be metastasis inhibition effective.

13. The method according to claim 12, wherein the cancer is carcinoma.

14. The method according to claim 13, wherein the carcinoma is melanoma, colon cancer or rectal cancer.

15. The method according to claim 12, wherein chemotherapy comprises treatment with alkylating agents, antimetabolites, plant alkaloids, topoisomerase inhibitors or antitumour agents.

16. The method according to claim 15, wherein the chemotherapy comprises treatment with antimetabolites.

17. The method according to claim 16, wherein the antimetabolite is 5-fluorouracil, fludarabine, or methotrexate.

18. The method according to claim 17, wherein the antimetabolite is 5-fluorouracil.

* * * * *

SEQUENCE LISTING

```
<160> NUMBER OF SEQ ID NOS: 11

<210> SEQ ID NO 1
<211> LENGTH: 261
<212> TYPE: DNA
<213> ORGANISM: Homo sapiens

<400> SEQUENCE: 1
gaacaagact gtatgtttgg gaatgggaaa ggataccggg gcaagaaggc aaccactgtt      60
actgggacgc catgccagga atgggctgcc caggagcccc atagacacag cacgttcatt     120
ccagggacaa ataaatgggc aggtctggaa aaaaattact gccgtaaccc tgatggtgac     180
atcaatggtc cctggtgcta cacaatgaat ccaagaaaac tttttgacta ctgtgatatc     240
cctctctgtg catcctctta a                                              261

<210> SEQ ID NO 2
<211> LENGTH: 86
<212> TYPE: PRT
<213> ORGANISM: Homo sapiens
```

-continued

<400> SEQUENCE: 2

Glu Gln Asp Cys Met Phe Gly Asn Gly Lys Gly Tyr Arg Gly Lys Lys
1               5                   10                  15

Ala Thr Thr Val Thr Gly Thr Pro Cys Gln Glu Trp Ala Ala Gln Glu
            20                  25                  30

Pro His Arg His Ser Thr Phe Ile Pro Gly Thr Asn Lys Trp Ala Gly
        35                  40                  45

Leu Glu Lys Asn Tyr Cys Arg Asn Pro Asp Gly Asp Ile Asn Gly Pro
    50                  55                  60

Trp Cys Tyr Thr Met Asn Pro Arg Lys Leu Phe Asp Tyr Cys Asp Ile
65                  70                  75                  80

Pro Leu Cys Ala Ser Ser
                85

<210> SEQ ID NO 3
<211> LENGTH: 255
<212> TYPE: DNA
<213> ORGANISM: Homo sapiens

<400> SEQUENCE: 3
atgagatttc cttcaatttt tactgcagtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc cattttccaa cagcacaaat     180
aacgggttat tgtttataaa tactactatt gccagcattg ctgctaaaga agaagggta     240 tctctcgaga aaaga                                                     255

<210> SEQ ID NO 4
<211> LENGTH: 85
<212> TYPE: PRT
<213> ORGANISM: Homo sapiens

<400> SEQUENCE: 4

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg
                85

<210> SEQ ID NO 5
<211> LENGTH: 34
<212> TYPE: DNA
<213> ORGANISM: Artificial Sequence
<220> FEATURE:
<223> OTHER INFORMATION: Primer

<400> SEQUENCE: 5
tccgctcgag aaaagagaac aagactgtat gttt                                  34

<210> SEQ ID NO 6
<211> LENGTH: 31

-continued

```
<212> TYPE: DNA
<213> ORGANISM: Artificial Sequence
<220> FEATURE:
<223> OTHER INFORMATION: Primer

<400> SEQUENCE: 6
cgaattctta agaggatgca cagagaggga t                                      31

<210> SEQ ID NO 7
<211> LENGTH: 6
<212> TYPE: PRT
<213> ORGANISM: Homo sapiens

<400> SEQUENCE: 7

Glu Gln Asp Cys Met Phe
1               5

<210> SEQ ID NO 8
<211> LENGTH: 29
<212> TYPE: DNA
<213> ORGANISM: Artificial Sequence
<220> FEATURE:
<223> OTHER INFORMATION: Primer

<400> SEQUENCE: 8
tccatatgaa agccctgtg gtccaggat                                          29

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
cgggatcctt aagaggatgc aca                                               23

<210> SEQ ID NO 10
<211> LENGTH: 924
<212> TYPE: DNA
<213> ORGANISM: Homo sapiens

<400> SEQUENCE: 10
aaaagccctg tggtccagga ttgctaccat ggtgatggac ggagttatcg aggcatatcc        60
tccaccactg tcacaggaag gacctgtcaa tcttggtcat ctatgatacc acactggcat       120
cagaggaccc cagaaaacta cccaaatgct ggcctgaccg agaactactg caggaatcca       180
gattctggga acaaccctg gtgttacaca accgatccgt gtgtgaggtg ggagtactgc        240
aatctgacac aatgctcaga acagaatca ggtgtcctag agactccac tgttgttcca        300 gttccaagca tggaggctca ttctgaagca gcaccaactg agcaaacccc tgtggtccgg       360
cagtgctacc atggtaatgg ccagagttat cgaggcacat tctccaccac tgtcacagga       420
aggacatgtc aatcttggtc atccatgaca ccacaccggc atcagaggac cccagaaaac       480
tacccaaatg atggcctgac aatgaactac tgcaggaatc cagatgccga tacaggccct       540
tggtgtttta ccacggaccc cagcatcagg tgggagtact gcaacctgac gcgatgctca       600
gacacagaag ggactgtggt cgctcctccg actgtcatcc aggttccaag cctagggcct       660
ccttctgaac aagactgtat gtttgggaat gggaaggat accggggcaa gaaggcaacc       720
actgttactg gacgccatg ccaggaatgg gctgcccagg agccccatag acacagcacg       780
ttcattccag ggacaaataa atgggcaggt ctggaaaaaa attactgccg taaccctgat       840
```

-continued

```
ggtgacatca atggtccctg gtgctacaca atgaatccaa gaaaactttt tgactactgt    900
gatatccctc tctgtgcatc ctct                                           924
```

<210> SEQ ID NO 11
<211> LENGTH: 308
<212> TYPE: PRT
<213> ORGANISM: Homo sapiens

<400> SEQUENCE: 11

```
Lys Ser Pro Val Val Gln Asp Cys Tyr His Gly Asp Gly Arg Ser Tyr
1               5                   10                  15

Arg Gly Ile Ser Ser Thr Thr Val Thr Gly Arg Thr Cys Gln Ser Trp
            20                  25                  30

Ser Ser Met Ile Pro His Trp His Gln Arg Thr Pro Glu Asn Tyr Pro
        35                  40                  45

Asn Ala Gly Leu Thr Glu Asn Tyr Cys Arg Asn Pro Asp Ser Gly Lys
    50                  55                  60

Gln Pro Trp Cys Tyr Thr Thr Asp Pro Cys Val Arg Trp Glu Tyr Cys
65                  70                  75                  80

Asn Leu Thr Gln Cys Ser Glu Thr Glu Ser Gly Val Leu Glu Thr Pro
                85                  90                  95

Thr Val Val Pro Val Pro Ser Met Glu Ala His Ser Glu Ala Ala Pro
            100                 105                 110

Thr Glu Gln Thr Pro Val Val Arg Gln Cys Tyr His Gly Asn Gly Gln
        115                 120                 125

Ser Tyr Arg Gly Thr Phe Ser Thr Thr Val Thr Gly Arg Thr Cys Gln
    130                 135                 140

Ser Trp Ser Ser Met Thr Pro His Arg His Gln Arg Thr Pro Glu Asn
145                 150                 155                 160

Tyr Pro Asn Asp Gly Leu Thr Met Asn Tyr Cys Arg Asn Pro Asp Ala
                165                 170                 175

Asp Thr Gly Pro Trp Cys Phe Thr Thr Asp Pro Ser Ile Arg Trp Glu
            180                 185                 190

Tyr Cys Asn Leu Thr Arg Cys Ser Asp Thr Glu Gly Thr Val Val Ala
        195                 200                 205

Pro Pro Thr Val Ile Gln Val Pro Ser Leu Gly Pro Pro Ser Glu Gln
    210                 215                 220

Asp Cys Met Phe Gly Asn Gly Lys Gly Tyr Arg Gly Lys Lys Ala Thr
225                 230                 235                 240

Thr Val Thr Gly Thr Pro Cys Gln Glu Trp Ala Ala Gln Glu Pro His
                245                 250                 255

Arg His Ser Thr Phe Ile Pro Gly Thr Asn Lys Trp Ala Gly Leu Glu
            260                 265                 270

Lys Asn Tyr Cys Arg Asn Pro Asp Gly Asp Ile Asn Gly Pro Trp Cys
        275                 280                 285

Tyr Thr Met Asn Pro Arg Lys Leu Phe Asp Tyr Cys Asp Ile Pro Leu
    290                 295                 300

Cys Ala Ser Ser
305
```